US008546321B2

(12) United States Patent
Bock et al.

(10) Patent No.: US 8,546,321 B2
(45) Date of Patent: Oct. 1, 2013

(54) IL-4-DERIVED PEPTIDES FOR MODULATION OF THE CHRONIC INFLAMMATORY RESPONSE AND TREATMENT OF AUTOIMMUNE DISEASES

(75) Inventors: Elisabeth Bock, Charlottenlund (DK); Vladimir Berezin, Copenhagen N (DK)

(73) Assignee: Kobenhavns Universitet (DK)

( * ) Notice: Subject to any disclaimer, the term of this patent is extended or adjusted under 35 U.S.C. 154(b) by 0 days.

(21) Appl. No.: 13/127,574

(22) PCT Filed: Nov. 17, 2009

(86) PCT No.: PCT/DK2009/050304
§ 371 (c)(1), (2), (4) Date: Jun. 14, 2011

(87) PCT Pub. No.: WO2010/054667
PCT Pub. Date: May 20, 2010

(65) Prior Publication Data
US 2011/0300148 A1 Dec. 8, 2011

(30) Foreign Application Priority Data
Nov. 17, 2008 (DK) ................................ 2008 01601

(51) Int. Cl.
*A61K 38/00* (2006.01)
*A61K 38/03* (2006.01)

(52) U.S. Cl.
USPC .......... 514/1.1; 514/16.6; 514/21.4; 514/21.5

(58) Field of Classification Search
None
See application file for complete search history.

(56) References Cited

U.S. PATENT DOCUMENTS 6,337,072 B1 * 1/2002 Ford et al. .................. 424/198.1
2003/0056244 A1 * 3/2003 Huang et al. .................. 800/278
2006/0241286 A1 10/2006 Zagury

FOREIGN PATENT DOCUMENTS

WO WO 91/09059 6/1991
WO WO 00/73460 12/2000

OTHER PUBLICATIONS

Wells, 1990, Biochemistry 29:8509-8517.*
Ngo et al., 1994, The Protein Folding Problem and Tertiary Structure Prediction, Merz et al., eds., Birkhauser, Boston, pp. 492- 495.*
Tokuriki et al., 2009, Curr. Opin. Struc. Biol. 19:596-604.*
Agnello, Davide et al., "Cytokines and Transcription Factors That Regulate T Helper Cell Differentiation: New Players and New Insights," Journal of Clinical Immunology, vol. 23, No. 3, May 2003, pp. 147-161.
Hage, Thorsten et al., "Crystal Structure of the Interleukin-4/Receptor α Chain Complex Reveals α Mosaic Binding Interface," Cell, vol. 97, Apr. 1999, pp. 271-281.
He, Bei Ping et al., "Activated microglia (BV-2) facilitation of TNF-α-mediated motor neuron death in vitro," Journal of Neuroimmunology 128, 2002, pp. 31-38.
Izuhara, K., et al., "IL-4 and IL-13 : Their Pathological Roles in Allergic Diseases and their Potential in Developing New Therapies," Current Drug Targets—Inflammation & Allergy, 2002, 1, pp. 263-269.
LaPorte, Sherry L., et al., "Molecular and structural basis of cytokine receptor pleiotropy in the Interleukin-4/13 system," Cell, 2008, 132(2), pp. 259-272.
Leach, Michael W., et al., "Safety Evaluation of Recombinant Human Interleukin-4, II. Clinical Studies," Clinical Immunology and Immunopathology, vol. 83, No. 1, 1997, pp. 12-14.
Martin, Roland, "Interleukin 4 treatment of psoriasis: are pleiotropic cytokines suitable therapies for autoimmune diseases?" TRENDS in Pharmacological Sciences, vol. 24, No. 12, 2003, pp. 613-616.
Martinez, Fernando Oneissi, et al., "Macrophage activation and polarization," Frontiers in Bioscience 13, 2008, pp. 453-461.
Müller, Thomas et al., "Human Interleukin-4 and Variant R88Q: Phasing X-ray Diffraction Data by Molecular Replacement Using X-ray and Nuclear Magnetic Resonance Models," J. Mol. Biol. 1995, 247, pp. 360-372.
Neiiendam, Johanne Louise, et al., "An NCAM-derived FGF-receptor agonist, the FGL-peptide, induces neurite outgrowth and neuronal survival in primary rat neurons," Journal of Neurochemistry, 2004, 91, pp. 920-935.
Ryan, Lisa K., et al., "Characterization of Proinflammatory Cytokine Production and CD14 Expression by Murine Alveolar Macrophage Cell Lines," In Vitro Cell, Dev. Biol.—Animal 33, 1997, pp. 647-653.
Rønn, Lars C.B., et al., "A simple procedure for quantification of neurite outgrowth based on stereological principles," Journal of Neuroscience Methods 100, 2000, pp. 25-32.
Soroka, Vladislav et al., "Induction of Neuronal Differentiation by a Peptide Corresponding to the Homophilic Binding Site of the Second Ig Module of the Neural Cell Adhesion Molecule," The Journal of Biological Chemistry, 2002, vol. 277, No. 27, pp. 24676-24683.
Szegedi, Andrea et al., "Elevated rate of Thelperl ($T_H1$) lymphocytes and serum IFN-γ levels in psoriatic patients," Immunology Letters 86, 2003, pp. 277-280.
Whitehead, Robert P., et al., "Phase II Trial of Recombinant Human Interleukin-4 in Patients with Disseminated Malignant Melanoma: A Southwest Oncology Group Study," Journal of Immunotherapy, 21, 1998, pp. 440-446.
Zhang, Xinmin et al., The olfactory receptor gene superfamily of the mouse, Nature Neuroscience, vol. 5, No. 2, 2002, pp. 124-133.

* cited by examiner

*Primary Examiner* — Elizabeth C Kemmerer
(74) *Attorney, Agent, or Firm* — McLane, Graf, Raulerson & Middleton, PA

(57) ABSTRACT

The present invention relates to small peptides derived from a cytokine, interleukin-4 (IL-4), capable of binding to the IL-4 receptors and inhibiting macrophage activation, and thereby preventing the onset of inflammatory response. The invention further relates to use of said peptides for the production of a medicament for the treatment of different pathological conditions, wherein IL-4 plays a prominent role.

15 Claims, 17 Drawing Sheets

IL-4-DERIVED PEPTIDES FOR MODULATION OF THE CHRONIC INFLAMMATORY RESPONSE AND TREATMENT OF AUTOIMMUNE DISEASES

FIELD OF INVENTION

The present invention relates to small peptides derived from a cytokine, interleukin-4 (IL-4), capable of binding to the IL-4 receptors and inhibiting macrophage activation, and thereby preventing the onset of inflammatory response. The invention further relates to use of said peptides for the production of a medicament for the treatment of different pathological conditions, wherein IL-4 plays a prominent role.

BACKGROUND OF INVENTION

Abnormalities associated with inflammation comprise a large, unrelated group of disorders which underlie a variety of human diseases. Examples of disorders associated with inflammation include asthma, chronic inflammation, and autoimmune diseases including rheumatoid arthritis. Chronic inflammation is a pathological condition characterised by concurrent active inflammation, tissue destruction, and attempts at repair. Rheumatoid arthritis (RA) is a chronic, systemic autoimmune disorder that causes the immune system to attack the joints, where it causes inflammation (arthritis) and destruction. It can also damage some organs, such as the lungs and skin. It can be a disabling and painful condition, which can lead to substantial loss of functioning and mobility. It is diagnosed with blood tests (especially a test called rheumatoid factor) and X-rays.

The inflammatory reaction observed in autoimmune disease involves both cellular and soluble players. The cause of RA is not known. It involves complex interactions of various cells, cytokines and enzymes. The disease begins when an inciting antigen gains access to the joint, triggering an immune response. The antigenic stimulus activates CD4+ lymphocytes (T-cells). Once CD4+ T-cells become activated, a complex cascade of biological events take place including stimulation of macrophages, B-cells, fibroblasts, chondrocytes and osteoclasts. Activated macrophages secrete cytokines, such as interleukin-1 (IL-1), IL-6, IL-8, IL-15 and tumor necrosis factor-α (TNF-α) (Martinez et al., 2008).

Interleukin-4 (IL-4) is secreted by CD4+ T-cells (Th2 cells). It is a pleiotropic cytokine, acting on various cell types and tissues. Its action on immune cells results in activation and growth of B cells, IgG and IgE production, MHC class II induction, growth and survival of T cells, Th2 differentiation, enhancement of mast cell growth, enhancement of IL-2 and IL-12-induced interferon-γ (INF-γ) secretion in NK cells, downregulation of C5a and C3a in monocytes and Mo-derived dendritic cells and inhibition of macrophage activation (Agnello et al., 2003; Szehedi et al., 2003; Roland, 2003).

The structure of recombinant human IL-4 has been determined by both NMR and X-ray diffraction methods in several laboratories. It has a classical 4 helix bundle cytokine structure (Muller et al., 1995). IL-4, like other cytokines, exerts its biological activity by binding to the receptors on the cell surface. One receptor complex is composed of two components, the IL-4R α chain (IL-4Rα) and the IL-2R γ chain (γc, shared by the cytokines IL-2, IL-7, IL-9, IL-15 and IL-21), denoted type I IL-4R, whereas the other receptor complex is composed of IL-4Rα and the IL13 α chain (IL-13Rα1), called type II IL-4R. As γ c is expressed on most hematopoietic and immune cells, IL-4 is assumed to act on these cells through type I IL-4R. In contrast, expression of IL-13Rα1 is limited to some lineages such as B cells in hematopoietic and immune cells, but ubiquitously detected on non-immune cells (Izuhara et al., 2002). Thus IL4 acts on non-immune cells through type II IL-4R/IL-13R.

Binding IL-4 to its receptor a chain (IL-4Ra) is a crucial event for the generation of a Th2-dominated early immune response. The crystal structure of the intermediate complex between human IL-4 and IL4-BP was determined at 2.3 Å Resolution (PDB ID: 1IAR). It reveals a novel spatial orientation of the two proteins, a small but unexpected conformational change in the receptor-bound IL-4, and an interface with three separate clusters of trans-interacting residues (Hage et al., 1999). Crystal structure of the Il4-Il4r-common gamma ternary complex has recently been solved (PDB ID: 3BPL; LaPorte et al., 2008).

Recombinant IL-4 has been through several clinical trials. IL-4 has been shown to be beneficial in patients with psoriasis, effectively correcting imbalances in immune functions (Martin 2003). The safety and tolerability of *Escherichia coli*-derived recombinant human interleukin-4 (rhuIL-4) have been evaluated in phase I and phase II studies in human patients with a variety of malignancies. Clinical trials have demonstrated that subcutaneous administration of rhuIL-4 is safe and well tolerated at doses as high as 5 μg/kg/day and as high as 10 μg/kg when administered 3 times/week. Although preclinical safety studies in cynomolgus monkeys demonstrated a number of adverse effects following repeated daily dosing with rhuIL-4, similar effects have generally not been observed in human patients (Leach et al., 1997). The most common toxicities were elevated liver function tests, nausea/vomiting/diarrhea, malaise/fatigue, edema, headache, myalgias/arthralgias, and fever/chills. Despite promising preclinical growth inhibitory and immunomodulatory effects, IL-4 in this dose and schedule showed only low antitumor activity (Whitehead et al., 1998).

Many human autoimmune and inflammatory diseases are still treated by a combination of corticosteroids and general immunosuppression. A better understanding of the pathogenesis of these diseases has led to therapies that are more specific. Among these, the recombinant humanized proteins are considered as the future therapies. However, drugs based on recombinant proteins have several disadvantages including high production cost, big batch-to-batch variation and denaturation during storage.

SUMMARY OF INVENTION

The present invention concerns fragments of IL-4 that can be chemically synthesized and used as functional mimetics of IL-4.

The present invention relates to a compound comprising an isolated peptide consisting of at most 35 contiguous amino acid residues derived from IL-4 or a variant being at least 70% identical. A compound comprising such amino acid sequence is according to the invention capable of i) binding to the IL-4 receptor; ii) inhibiting an inflammatory response; iii) inhibiting macrophage activation; iii) activating B-cells; iv) activating growth and survival of T-cells; v) downregulating C5a and C3a in monocytes and dendritic cells, vi) modulating activity of the IL-4 receptor.

Accordingly, another aspect of the invention relates to use of compounds of the invention as medicaments and for the preparation of medicaments for treatment of a condition or disease wherein i) binding to the IL-4 receptor; ii) inhibiting an inflammatory response; iii) inhibiting macrophage activation; iii) activating B-cells; iv) activating growth and survival of T-cells; v) downregulating C5a and C3a in monocytes and dendritic cells, vi) modulating activity of the IL-4 receptor is part of said treatment.

Still, in another aspect a peptide of the invention or a compound comprising the peptide may be used for the production of an antibody. Such antibodies will bind an epitope within a peptide of the invention.

The invention further relates to pharmaceutical compositions comprising a peptide of the invention, or an antibody capable of recognising an epitope within a peptide of the invention.

The invention also concerns a method of treatment of conditions wherein i) binding to the IL-4 receptor; ii) inhibiting an inflammatory response; iii) inhibiting macrophage activation; iii) activating B-cells; iv) activating growth and survival of T-cells; v) downregulating C5a and C3a in monocytes and dendritic cells, vi) modulating activity of the IL-4 receptor is beneficial, said method comprising a step of administering a compound of the invention, antibody of the invention or a pharmaceutical composition comprising said peptide sequence, said compound or said antibody to an individual in need.

Figure 1:
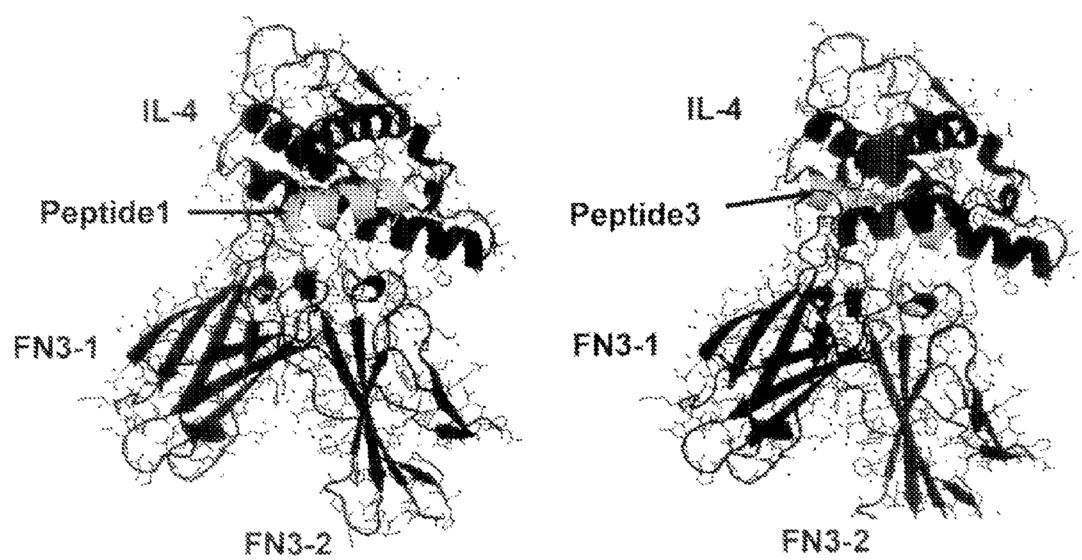
FIG. 1.

Structure of IL-4 in complex with the ectodomain of IL-4Rα (PDB ID: 1IAR). Location of peptide1 (SEQ ID NO:2) (left) and peptide3 (SEQ ID NO:3) (right) is indicated in grey.

FIG. 2.

Structure of IL-4 in complex with the ectodomain of IL-4Rα (PDB ID: 1IAR). Location of peptide3a (SEQ ID NO:1) (left) and peptide4 (SEQ ID NO: 4) (right) is indicated in grey.

FIG. 3.

Structure of IL-4 in complex with the ectodomain of γc common receptor (PDB ID: 3BPL). Location of peptide1 (SEQ ID NO:2) (left) and peptide3 (SEQ ID NO:3) (right) is indicated in grey.

FIG. 4

Structure of IL-4 in complex with the ectodomain of IL-4Rα and γc common receptor (PDB ID: 3BPL). Location of peptide3a (SEQ ID NO:1) (left) and peptide4 (SEQ ID NO: 4) (right) is indicated in grey.

FIG. 5.

Effect of IL-4-derived peptide Ph1 (SEQ ID NO:2) on neurite outgrowth in cultures of cerebellar granule neurons. The P2d peptide was used a positive control (see Soroka et al., 2002).

FIG. 6.

Effect of Ph2 (SEQ ID NO:3) on neurite outgrowth in cultures of cerebellar granule neurons. Level of significance compared to control is represented as followed: ***=p<0.001. Seven independent experiments were performed.

FIG. 7.

Macrophage secretion of TNF-α when pre-treated with Ph2 (SEQ ID NO:3).

A: Column diagram of the amount of TNF-α released from macrophages when not pre-treated with Ph2 or activated by IFN-γ (striped column), when activated with 0.01 μg/ml IFN-γ (white column) or when pre-treated with 100 μM hydrocortisone and activated with 0.01 μg/ml IFN-γ (black column). Level of significance compared to TNF-α amount released from non-pre-treated, activated macrophages (white column) are represented as followed: *=p<0.001. B: Column diagram of the amount of TNF-α released from macrophages when pre-treated with Ph2 in various concentrations before activation with 0.01 μg/ml IFN-γ. Level of significance compared to TNF-α amount released from non-pre-treated, activated macrophages (0 column) is represented as followed: *=p<0.001. Results in both figures are shown as percentages of the untreated control, only activated by IFN-γ. Results from six independent experiments are shown for the controls and the Ph2 concentrations 9, 27, 81 and 243 μg/ml.

FIG. 8.

Binding of Ph2 (SEQ ID NO:3) to IL4rα.

Binding study by applying Surface Plasmon Resonance. A: As a control, binding between IL4 and IL4rα was investigated by immobilizing IL4rα on a chip and then IL4 was run over the chip in solution. B: Binding between Ph2 and IL4rα was studied by immobilizing Ph2 on the chip and IL4rα was run over the chip in solution. Results were analysed and KD was calculated with the computer software BIAevaluation.

FIG. 9.

Effect of Ph3 (SEQ ID NO:1) on neurite outgrowth in cultures of cerebellar granule neurons. Level of significance compared to control is represented as followed: **=p<0.01. Seven independent experiments were performed.

FIG. 10.

Macrophage secretion of TNF-α when pre-treated with Ph3 (SEQ ID NO:1).

A: Column diagram of the amount of TNF-α released from macrophages when not pre-treated with Ph3 or activated by IFN-γ (striped column), when activated with 0.01 μg/ml IFN-γ (white column) or when pre-treated with 100 μM hydrocortisone and activated with 0.01 μg/ml IFN-γ (black column). Level of significance compared to TNF-α amount released from non-pre-treated, activated macrophages (white column) are represented as followed: *=p<0.001. B: Column diagram of the amount of TNF-α released from macrophages when pre-treated with Ph3 in various concentrations before activation with 0.01 μg/ml IFN-γ. Level of significance compared to TNF-α amount released from non-pre-treated, activated macrophages (0 column) is represented as followed: *=p<0.001. Results in both figures are shown as percentages of the untreated control, only activated by IFN-γ. Results from six independent experiments are shown for the controls and the Ph3 concentrations 9, 27, and 81 μg/ml.

FIG. 11.

Binding of Ph3 (SEQ ID NO:1) to IL4rα.

Binding study by applying Surface Plasmon Resonance. A: As a control, binding between IL4 and IL4rα was investigated by immobilizing IL4rα on a chip and then IL4 was run over the chip in solution. B: Binding between Ph3 and IL4rα was studied by immobilizing Ph3 on the chip and IL4rα was run over the chip in solution. Results were analysed and KD was calculated with the computer software BIAevaluation.

FIG. 12.

Effect of Ph4 (SEQ ID NO:4) on neurite outgrowth in cultures of cerebellar granule neurons. Level of significance compared to control is represented as followed: *=p<0.05, **=p<0.01. Five independent experiments were performed.

FIG. 13.

Macrophage secretion of TNF-α when pre-treated with Ph5 (SEQ ID NO:5).

A: Column diagram of the amount of TNF-α released from macrophages when not pre-treated with Ph4 or activated by IFN-γ (stripes), when activated with 0.01 μg/ml IFN-γ (white) and when pre-treated with 100 μM hydrocortisone and activated with 0.01 μg/ml IFN-γ (black). B: Column diagram of the amount of TNF-α released from macrophages when pre-treated with 9 μg/ml Ph5 before activation with 0.01 μg/ml IFN-γ. Two independent experiments were performed.

FIG. 14.

Macrophage secretion of TNF-α when pre-treated with Ph6 (SEQ ID NO:6).

A: Column diagram of the amount of TNF-α released from macrophages when not pre-treated with Ph4 or activated by IFN-γ (stripes), when activated with 0.01 μg/ml IFN-γ (white) and when pre-treated with 100 μM hydrocortisone and activated with 0.01 μg/ml IFN-γ (black). B: Column diagram of the amount of TNF-α released from macrophages when pre-treated with various concentrations of Ph6 before activation with 0.01 μg/ml IFN-γ. Two independent experiments were performed.

FIG. 15.

Macrophage secretion of TNF-α when pre-treated with Ph8 (SEQ ID NO:1).

A: Column diagram of the amount of TNF-α released from macrophages when not pre-treated with Ph3 or activated by IFN-γ (striped column), when activated with 0.01 μg/ml IFN-γ (white column) or when pre-treated with 100 μM hydrocortisone and activated with 0.01 μg/ml IFN-γ (black column). Level of significance compared to TNF-α amount released from non-pre-treated, activated macrophages (white column) are represented as followed: *=p<0.001. B: Column diagram of the amount of TNF-α released from macrophages when pre-treated with Ph8 in various concentrations before activation with 0.01 μg/ml IFN-γ. Level of significance compared to TNF-α amount released from non-pre-treated, activated macrophages (0 column) is represented as followed: *=p<0.001. Results in both figures are shown as percentages of the untreated control, only activated by IFN-γ. Results from six independent experiments are shown for the controls and the Ph8 concentrations 9, 27, 81 and 243 μg/ml.

FIG. 16.

Macrophage secretion of TNF-α when pre-treated with Ph10 (SEQ ID:1).

A: Column diagram of the amount of TNF-α released from macrophages when not pre-treated with Ph10 or activated by IFN-γ (striped column), when activated with 0.01 μg/ml IFN-γ (white column) or when pre-treated with 100 μM hydrocortisone and activated with 0.01 μg/ml IFN-γ (black column). Level of significance compared to TNF-α amount released from non-pre-treated, activated macrophages (white column) are represented as followed: =p<0.01. B: Column diagram of the amount of TNF-α released from macrophages when pre-treated with Ph10 in various concentrations before activation with 0.01 μg/ml IFN-γ. Level of significance compared to TNF-α amount released from non-pre-treated, activated macrophages (0 column) is represented as followed: =p<0.01. Results in both figures are shown as percentages of the untreated control, only activated by IFN-γ. Results from four independent experiments are shown for the controls and the Ph10 concentrations 9, 27, 81 and 243 μg/ml. Only two experiments were performed with the concentration 54 μg/ml Ph10 which does that these data were not included in the statistical analysis.

FIG. 17.

Macrophage secretion of TNF-α when pre-treated with Ph12 (SEQ ID:19).

A: Column diagram of the amount of TNF-α released from macrophages when not pre-treated with Ph12 or activated by IFN-γ (stripes), when activated with 0.01 μg/ml IFN-γ (white) and when pre-treated with 100 μM hydrocortisone and activated with 0.01 μg/ml IFN-γ (black). B: Column diagram of the amount of TNF-α released from macrophages when pre-treated with Ph12 in various concentrations before activation with 0.01 μg/ml IFN-γ. Two independent experiments were performed.

DETAILED DESCRIPTION OF THE INVENTION

A compound according to the invention can be a fragment derived from interleukin-4, or it may be derived from a variant of interleukin-4, such as a natural or recombinant interleukin-4 variant, for example a interleukin-4 variant produced by alternative splicing, or genetic polymorphism, or any type of recombinant interleukin-4.

A peptide according to the invention is a peptide which is capable of interacting with the IL-4 receptor, modulating IL-4 receptor signalling, activating B-cells, activating growth and survival of T-cells, downregulating C5a and C3a in monocytes and dendritic cells or inhibiting macrophage activation.

By the terms “modulation” or “modulating” are meant a change, such as an inhibition or stimulation. By the term “interacting” is meant an action, such as binding, between the peptide and the IL-4 receptor which cause an effect.

Amino Acid Sequence

Compounds according to the invention comprise a peptide consisting of a contiguous amino acid sequence derived from IL-4 or a fragment or variant thereof.

In one embodiment the compound according to the invention may comprise a peptide consisting of at most 35 contiguous amino acids which is derived from interleukin-4 (SEQ ID:38) or a fragment thereof, or a variant being at least 70% identical to SEQ ID NO:38 or a fragment thereof.

The amino acid sequence of the human IL-4 precursor (Swiss-Prot ID: P05112) is:

```
                                          (SEQ ID NO: 38)
MGLTSQLLPP LFFLLACAGN FVHGHKCDIT LQEIIKTLNS

LTEQKTLCTE LTVTDIFAAS KNTTEKETFC RAATVLRQFY

SHHEKDTRCL GATAQQFHRH KQLIRFLKRL DRNLWGLAGL

NSCPVKEANQ STLENFLERL KTIMREKYSK CSS
```

A peptide sequence according to the invention consists of at most 35 contiguous amino acid residues, such as from 3 to 35 amino acid residues, such as from 3 to 30, for example from 3 to 25, such as from 5 to 25, such as form 7 to 25, such as from 8 to 25, for example from 10 to 25, or from 12 to 25, such as from 14 to 25. Sequences comprising from 5 to 25 contiguous amino acid residues are preferred.

In a preferred embodiment said peptides of the invention comprise at most 35 contiguous amino acids which are derived from an alpha-helix of IL-4.

By the term “alpha-helix” is meant the common motif in the secondary structure of proteins, the alpha helix (α-helix) is a right- or left-handed coiled conformation, in which every backbone N—H group donates a hydrogen bond to the backbone C═O group of the amino acid four residues earlier.

In a preferred embodiment said peptides of the invention comprise a sequence with the formula X1-X2-X3, wherein X1 is L, X2 is I, Q, G, T, or a charged amino acid; and X3 is Q, T, or a charged amino acid.

In one preferred embodiment X2 is I or Q.

In a more preferred embodiment X2 is I.

In another more preferred embodiment X2 is Q.

In one preferred embodiment X2 is a charged amino acid.

In a preferred embodiment X3 is a charged amino acid.

In a more preferred embodiment X3 is R or E.

In one most preferred embodiment X3 is R.

In another more preferred embodiment X3 is E.

In another preferred embodiment X3 is Q or T.

In an even more preferred embodiment X1 is L, X2 is I, and X3 is R.

In another even more preferred embodiment X1 is L, X2 is Q and X3 is E.

In a most preferred embodiment said peptides of the invention consist of an amino acid sequence selected from one of the following amino acid sequences:

| | |
|---|---|
| AQFHRHKQLIRFLKRA | SEQ ID NO: 1 |
| AITLQEIIKTLNSA | SEQ ID NO: 2 |
| ARFLKRLDRNLWGG | SEQ ID NO: 3 |
| AERLKTIMREKYSKS | SEQ ID NO: 4 |
| LQEIKTLN | SEQ ID NO: 5 |
| KRLQQNLFGG | SEQ ID NO: 6 |
| Ac-AQFHRHKQLIRFLKRA | SEQ ID NO: 7 |
| QEIIKKL | SEQ ID NO: 8 |
| AIQNQEEIKYLNS | SEQ ID NO: 9 |
| AIILQEI | SEQ ID NO: 10 |
| IVLQEII | SEQ ID NO: 11 |
| TLGEIIKGVNS | SEQ ID NO: 12 |
| VTLIDHSEEIFKTLN | SEQ ID NO: 13 |
| LQERIKSLN | SEQ ID NO: 14 |
| RLDRENVAVYNLW | SEQ ID NO: 15 |
| LRSLDRNL | SEQ ID NO: 16 |
| RLLRLDRN | SEQ ID NO: 17 |
| RFLKRYFYNLEENL | SEQ ID NO: 18 |
| RNKQVIDSLAKFLKR | SEQ ID NO: 19 |
| RHKALIR | SEQ ID NO: 20 |
| KKLIRYLK | SEQ ID NO: 21 |
| RHKTLIR | SEQ ID NO: 22 |
| MQDKYSKS | SEQ ID NO: 23 |
| AERVKIEQREYKKYS | SEQ ID NO: 24 |
| SQLIRFLKRLA | SEQ ID NO: 25 |
| TVTDIFAASKNTT | SEQ ID NO: 26 |
| TLENFLERLKTA | SEQ ID NO: 27 |
| TEKEVLRQFYSA | SEQ ID NO: 28 |
| KTLTELTKTLNS | SEQ ID NO: 29 |
| AHKEIIKTLNSLQKA | SEQ ID NO: 30 |
| AKTLSTELTVTA | SEQ ID NO: 31 |
| STLENFLERLA | SEQ ID NO: 32 |

-continued

| | |
|---|---|
| NEERLKTIMRA | SEQ ID NO: 33 |
| RAATVLRQFYSR | SEQ ID NO: 34 |
| KTLNSLTEQKT | SEQ ID NO: 35 |
| AHRHKQLIRA | SEQ ID NO: 36 |
| ATAQQFHRHKQA | SEQ ID NO: 37 |

or a variant or fragment thereof.

In one embodiment the said peptides of the invention consist of an amino acid sequence selected from one of the following amino acid sequences:

| | |
|---|---|
| AQFHRHKQLIRFLKRA | (SEQ ID NO: 1) |
| Ac-AQFHRHKQLIRFLKRA | (SEQ ID NO: 7) |
| RHKALIR | (SEQ ID NO: 20) |
| KKLIRYLK | (SEQ ID NO: 21) |
| RHKTLIR | (SEQ ID NO: 22) |
| SQLIRFLKRLA | (SEQ ID NO: 25) |
| AHRHKQLIRA | (SEQ ID NO: 36) |

or a variant or fragment thereof.

In one embodiment the said peptides of the invention consist of an amino acid sequence selected from one of the following amino acid sequences:

| | |
|---|---|
| AITLQEIIKTLNSA | (SEQ ID NO: 2) |
| LQEIKTLN | (SEQ ID NO: 5) |
| AIILQEI | (SEQ ID NO: 10) |
| IVLQEII | (SEQ ID NO: 11) |
| LQERIKSLN | (SEQ ID NO: 14) |
| AHKEIIKTLNSLQKA | (SEQ ID NO: 30) |

or a variant or fragment thereof.

In the present context the standard one-letter code for amino acid residues as well as the standard three-letter code are applied. Abbreviations for amino acids are in accordance with the recommendations in the IUPAC-IUB Joint Commission on Biochemical Nomenclature Eur. J. Biochem, 1984, vol. 184, pp 9-37. Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a peptide for use according to the invention exists as the free carboxylic acid, this may also be specified as "—OH". However, the C-terminal amino acid of a peptide for use according to the invention may be the amidated derivative, which is indicated as "—$NH_2$". Where nothing else is stated the N-terminal amino acid of a polypeptide comprises a free amino-group, this may also be specified as "H—".

A peptide, fragment or variant thereof according to the invention can also comprise one or several unnatural amino acids.

A preferred peptide according to the invention is an isolated contiguous peptide sequence which comprises at most 35 amino acid residues of IL-4. It is understood that all peptides according to the invention comprise at least one amino acid sequence selected from any of the sequences SEQ ID NOs: 1-37 or a fragment or variant thereof.

Thus, some embodiments of the invention may relate to a peptide comprising a fragment of a sequence selected from SEQ ID NOs:1 to 37. Another embodiment may relate to variants of SEQ ID NOs:1-37.

In one embodiment a variant fragment varies compared to a fragment of SEQ ID NO 38. A variant fragment may differ from a fragment of SEQ ID NO 38 by having a different amino acid at one or more positions. Preferably the variant differs from the fragment of SEQ ID NO 38 at up to 10 amino acid positions, more preferably at up to 8 position, such as up to 6 positions, for example up to 5 positions, such as at 4, 3, 2 or 1 position. Such variants may also differ from a fragment of SEQ ID NO 38 in other ways, such as by having one or more chemical modifications.

A variant according to the invention of an amino acid sequence selected from the sequences SEQ ID NOs: 1-38 may be i) an amino acid sequence which has at least 70% identity with a selected sequence, such as 71-75% identity, for example 76-80% identity, such as 81-85% identity, such as 86-90% identity, for example 91-95% identity, such as 96-99% identity, wherein the identity is defined as a percentage of identical amino acids in said sequence when it is collated with the selected sequence. The identity between amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90;

ii) an amino acid sequence which has at least 70% positive amino acid matches with a selected sequence, such as 71-80% positive amino acid matches, for example 81-85% positive amino acid matches, such as 86-90% positive amino acid matches, for example 91-95% positive amino acid matches, such as 96-99% positive amino acid matches, wherein the positive amino acid match is defined as the presence at the same position in two compared sequences of amino acid residues which has similar physical and/or chemical properties. Preferred positive amino acid matches of the present invention are K to R, E to D, L to M, Q to E, I to V, I to L, A to S, Y to W, K to Q, S to T, N to S and Q to R;

iii) an amino acid sequence which is identical to a selected sequence, or it has at least 70% identity with said sequence such as 71-80% identity, for example 81-85% identity, such as 86-90% identity, for example 91-95% identity, such as 96-99% identity, or has at least 75% positive amino acid matches with the selected sequence, such as 76-80% positive amino acid matches, for example 81-85% positive amino acid matches, such as 86-90% positive amino acid matches, for example 91-95% positive amino acid matches, such as 96-99% positive amino acid matches, and comprises other chemical moieties, e.g. phosphoryl, sulphur, acetyl, glycosyl moieties.

The term "variant of a peptide sequence" also means that the peptide sequence may be modified, for example by substitution of one or more of the amino acid residues. Both L-amino acids and D-amino acids may be used. Other modification may comprise derivatives such as esters, sugars, etc., for example methyl and acetyl esters, as well as polyethylene glycol modifications.

Furthermore, an amine group of the peptide may be converted to amides, wherein the acid part of the amide is a fatty acid.

In another aspect, variants of the amino acid sequences according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Val, Leu, and Ile, and independently thereof, variants, or fragments thereof, wherein at least one valine (Val) of said variant, or fragments thereof is substituted with an amino acid selected from the group of amino acids consisting of Gly, Ala, Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at least one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gin, and independently thereof, variants, or fragments thereof, wherein at least one aspargine (Asn) of said variants, or fragments thereof is substituted with an amino acid selected from the group of amino acids consisting of Asp, Glu, and Gin, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Gln, Ser, Thr, and Tyr.

It thus follows from the above that the same variant of a peptide fragment, or fragment of said variant may comprise more than one conservative amino acid substitution from more than one group of conservative amino acids as defined herein above. The term "conservative amino acid substitution" is used synonymously herein with the term "homologous amino acid substitution".

The groups of conservative amino acids are as the following:

A, G (neutral, weakly hydrophobic),
Q, N, S, T (hydrophilic, non-charged)
E, D (hydrophilic, acidic)
H, K, R (hydrophilic, basic)
L, P, I, V, M, F, Y, W (hydrophobic, aromatic)
C (cross-link forming)

Conservative substitutions may be introduced in any position of a preferred predetermined peptide for use according to the invention or fragment thereof. It may however also be desirable to introduce non-conservative substitutions, particularly, but not limited to, a non-conservative substitution in any one or more positions.

A non-conservative substitution leading to the formation of a variant fragment of the peptide for use according to the invention would for example differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gln or a charged amino acid such as Asp, Glu, Arg, or Lys, or substituting a charged or a polar residue for a non-polar one; and/or ii) differ substantially in its effect on peptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Substitution of amino acids may in one embodiment be made based upon their hydrophobicity and hydrophilicity values and the relative similarity of the amino acid side-chain substituents, including charge, size, and the like.

A peptide according to the invention is a peptide which is capable of interacting with the IL-4 receptor.

In one embodiment the peptide according to the invention is capable of modulating IL-4 receptor signalling.

In a preferred embodiment the peptide according to the invention is capable of stimulating IL-4 signalling. In another preferred embodiment the peptide according to the invention is capable of inhibiting IL-4 receptor signalling.

In another embodiment the peptide according to the invention is capable of activating B-cells.

In a further embodiment the peptide according to the invention is capable of activating growth and survival of T-cells.

In another embodiment the peptide according to the invention is capable of downregulating C5a and C3a in monocytes and dendritic cells.

In yet another embodiment the peptide according to the invention is capable of inhibiting macrophage activation.

Both fragments and variants of amino acid sequences according to the invention are functional equivalents of said sequences.

By the term "functional equivalent" of an amino acid sequence is in the present context meant a molecule which meets the criteria for a variant or a fragment of said amino acid sequence described above and which is capable of one or more functional activities of said sequence or a compound comprising said sequence. In a preferred embodiment, the functional equivalent of an amino acid sequence according to the invention, is capable of interacting with the IL-4 receptor and modulate IL-4 receptor signalling.

The invention relates both to isolated peptides according to the invention and fusion proteins comprising peptides according to the invention.

In one embodiment, the peptide according to the invention is an isolated peptide. By the term "isolated peptide" is meant that the peptide according to the invention is an individual compound and not a part of another compound. The isolated peptide may be produced by use of any recombinant technology methods or chemical synthesis and separated from other compounds, or it may be separated from a longer polypeptide or protein by a method of enzymatic or chemical cleavage and further separated from other protein fragments.

The peptide sequence may be present in the compound as a single copy, i.e. formulated as a monomer of the peptide sequence, or it may be present as several copies of the same sequence, e.g. as a multimer comprising two or more copies of a sequence selected from SEQ ID NOs:1-37, or two or more copies of a fragment or a variant of said sequence.

An isolated peptide according to the invention may in another embodiment comprise a fragment of interleukin-4 which consists of a contiguous amino acid sequence derived from interleukin-4, selected from SEQ ID NOs:1-37 or a variant thereof. In another embodiment the isolated peptide may consist of one or more of the sequences SEQ ID NOs: 1-37.

Production of Peptide Sequences

The peptide sequences of the present invention may be prepared by any conventional synthetic methods, recombinant DNA technologies, enzymatic cleavage of full-length proteins which the peptide sequences are derived from, or a combination of said methods.

Synthetic Preparation

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

Peptides may for example be synthesised by using Fmoc chemistry and with Acm-protected cysteins. After purification by reversed phase HPLC, peptides may be further processed to obtain for example cyclic or C- or N-terminal modified isoforms. The methods for cyclization and terminal modification are well-known in the art and described in detail in the above-cited manuals.

In a preferred embodiment the peptide sequences of the invention are produced synthetically, in particular, by the Sequence Assisted Peptide Synthesis (SAPS) method.

Peptides may be synthesised either batchwise in a polyethylene vessel equipped with a polypropylene filter for filtration or in the continuous-flow version of the polyamide solid-phase method (Dryland, A. and Sheppard, R. C., (1986) J. Chem. Soc. Perkin Trans. I, 125-137.) on a fully automated peptide synthesiser using 9-fluorenylmethyloxycarbonyl (Fmoc) or tert. -Butyloxycarbonyl, (Boc) as N-a-amino protecting group and suitable common protection groups for side-chain functionality's.

Recombinant Preparation

Thus, in one embodiment the peptides of the invention are produced by use of recombinant DNA technologies.

The DNA sequence encoding a peptide or the corresponding full-length protein the peptide originates from may be prepared synthetically by established standard methods, e.g. the phosphoamidine method described by Beaucage and Caruthers, 1981, Tetrahedron Lett. 22:1859-1869, or the method described by Matthes et al., 1984, EMBO J. 3:801-805. According to the phosphoamidine method, oligonucleotides are synthesised, e.g. in an automatic DNA synthesiser, purified, annealed, ligated and cloned in suitable vectors.

The DNA sequence encoding a peptide may also be prepared by fragmentation of the DNA sequences encoding the corresponding full-length protein of peptide origin, using DNAase I according to a standard protocol (Sambrook et al., Molecular cloning: A Laboratory manual. 2 rd ed., CSHL Press, Cold Spring Harbor, N.Y., 1989). The present invention relates to full-length proteins selected from the groups of proteins identified above. The DNA encoding the full-length proteins of the invention may alternatively be fragmented using specific restriction endonucleases. The fragments of DNA are further purified using standard procedures described in Sambrook et al., Molecular cloning: A Laboratory manual. 2 rd ed., CSHL Press, Cold Spring Harbor, N.Y., 1989.

The DNA sequence encoding a full-length protein may also be of genomic or cDNA origin, for instance obtained by preparing a genomic or cDNA library and screening for DNA sequences coding for all or part of the full-length protein by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al., 1988, Science 239:487-491.

The DNA sequence is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding a peptide or a full-length protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter (Subramani et al., 1981, Mol. Cell Biol. 1:854-864), the MT-1 (metallothionein gene) promoter (Palmiter et al., 1983, Science 222: 809-814) or the adenovirus 2 major late promoter. A suitable promoter for use in insect cells is the polyhedrin promoter (Vasuvedan et al., 1992, FEBS Lett. 311:7-11). Suitable promoters for use in yeast host cells include promoters from yeast glycolytic genes (Hitzeman et al., 1980, J. Biol. Chem. 255:12073-12080; Alber and Kawasaki, 1982, J. Mol. Appl. Gen. 1: 419-434) or alcohol dehydrogenase genes (Young et al., 1982, in Genetic Engineering of Microorganisms for Chemicals, Hollaender et al, eds., Plenum Press, New York), or the TPI1 (U.S. Pat. No. 4,599,311) or ADH2-4c (Russell et al., 1983, Nature 304: 652-654) promoters. Suitable promoters for use in filamentous fungus host cells are, for instance, the ADH3 promoter (McKnight et al., 1985, EMBO J. 4:2093-2099) or the tpiA promoter.

The coding DNA sequence may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op. cit.).

To obtain recombinant peptides of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-S-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or *Acharombacter lyticus*, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines are the HEK293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are described in e.g. Kaufman and Sharp, J. Mol. Biol. 159, 1982, pp. 601-621; Southern and Berg, 1982, J. Mol. Appl. Genet. 1:327-341; Loyter et al., 1982, Proc. Natl. Acad. Sci. USA 79: 422-426; Wigler et al., 1978, Cell 14:725; Corsaro and Pearson, 1981, in Somatic Cell Genetics 7, p. 603; Graham and van der Eb, 1973, Virol. 52:456; and Neumann et al., 1982, EMBO J. 1:841-845.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g. in catalogues of the American Type Culture Collection).

The peptides or full-length proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

Medicament

It is an objective of the invention to provide a compound capable of modulating the activity of IL-4, said compound according to the invention can be used as a medicament for the treatment of diseases, wherein modulation of IL-4 signalling may be considered as an essential condition for curing.

Accordingly, the invention relates to the use of one or more of the peptides comprising a sequence derived from IL-4 or a fragment or variant thereof for the manufacture of a medicament.

In one embodiment the medicament of the invention comprises at least one of the amino acid sequences set forth in SEQ ID NOS: 1-37 or fragments or variants of said sequences. In another embodiment the medicament of the invention comprises an antibody capable of binding to an epitope in IL-4 or a fragment thereof or a fragment or variant of said antibody.

The medicament of the invention comprises an effective amount of one or more of the compounds as defined above, or a composition comprising a compound as defined above, in combination with pharmaceutically acceptable additives. Such medicament may suitably be formulated for oral, percutaneous, subcutaneous, topical, intramuscular, intravenous, intracranial, intrathecal, intracerebroventricular, nasal, intranasal or pulmonal administration or parental administration supplemented with intraarticular administration into or near joint capsules.

Strategies in formulation development of medicaments and compositions based on the peptides of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration, e.g. inhalators and aerosols.

The active compound may be formulated as neutral or salt forms.

Pharmaceutically acceptable salts include acid addition salts (for example formed with the free amino groups of the peptide compound) and which are formed with inorganic acids such as, for example, hydrochloric, hydrobromic, hydroiodic, phosphoric, sulfuric, nitric acids and the like, or such organic acids as formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred μg active ingredient per administration with a preferred range of from about 0.1 μg to 5000 μg per kilo body weight. Using monomeric forms of the compounds, the suitable dosages are often in the range of from 0.1 μg to 5000 μg per kilo body weight, such as in the range of from about 0.1 μg to 3000 μg per kilo body weight, and especially in the range of from about 0.1 μg to 1000 μg per kilo body weight. Using multimeric forms of the compounds, the suitable dosages are often in the range of from 0.1 μg to 1000 μg per kilo body weight, such as in the range of from about 0.1 μg to 750 μg per kilo body weight, and especially in the range of from about 0.1 μg to 500 μg per kilo body weight such as in the range of from about 0.1 μg to 250 μg per kilo body weight. In particular when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For most indications a localised or substantially localised application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promotes delivery of the active substance to its target.

In many instances, it will be necessary to administrate the formulation multiple times. Administration may be a continuous infusion, such as intraventricular infusion or administration in more doses such as more times a day, daily, more times a week, weekly, etc. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

In connection with the use in nerve guides, the administration may be continuous or in small portions based upon controlled release of the active compound(s). Furthermore, precursors may be used to control the rate of release and/or site of release. Other kinds of implants and well as oral administration may similarly be based upon controlled release and/or the use of precursors.

As discussed above, the present invention relates to treatment of individuals for inducing differentiation, modulating proliferation, stimulate regeneration, neuronal plasticity and survival of cells in vitro or in vivo, the treatment involving administering an effective amount of one or more compounds as defined above.

Another strategy for administration is to implant or inject cells capable of expressing and secreting the compound in question. Thereby the compound may be produced at the location where it is going to act.

Treatment

The compounds according to the invention are particularly useful for treating inflammatory diseases and conditions. The compounds are useful for the diseases and conditions mentioned below, in particular useful for the treatment of inflammation in association with Rheumatoid arthritis and autoimmune diseases, as well as with Alzheimer's disease, Parkinson's disease and Huntington's disease.

Examples of disorders associated with inflammation that can be treated with the compounds of the invention include; neuroinflammation, Alzheimer's disease, Parkinson's disease and Huntington's disease, asthma and other allergic reactions, autoimmune diseases such as Acute disseminated encephalomyelitis (ADEM), Addison's disease, ALS, Ankylosing spondylitis, Antiphospholipid antibody syndrome (APS), Autoimmune hemolytic anemia, Autoimmune hepatitis, Autoimmune inner ear disease, Bullous pemphigoid, Coeliac disease, Chagas disease, Chronic obstructive pulmonary disease, Dermatomyositis, Diabetes mellitus type 1, Endometriosis, Goodpasture's syndrome, Graves' disease, Guillain-Barré syndrome (GBS), Hashimoto's disease, Hidradenitis suppurativa, Idiopathic thrombocytopenic purpura, Interstitial cystitis, Lupus erythematosus, Morphea, Multiple sclerosis, Myasthenia gravis, Narcolepsy, Neuromyotonia, Pemphigus Vulgaris, Pernicious anaemia, Polymyositis, Primary biliary cirrhosis, Rheumatoid arthritis, Schizophrenia, Scleroderma, Sjögren's syndrome, SLE, Temporal arteritis (also known as "giant cell arteritis"), Vasculitis, Vitiligo, Wegener's granulomatosis; chronic inflammation, chronic prostatitis, glomerulonephritis, hypersensitivities, inflammatory bowel diseases, pelvic inflammatory disease, reperfusion injury, rheumatoid arthritis, transplant rejection, vasculitis, osteoarthritis, tendovaginitis, and arthritis.

The treatment may also be of persistent acute inflammation due to non-degradable pathogens, persistent foreign bodies, or autoimmune reactions, inflammatory disease of the central nervous system, such as meningitis, encephalitis, inflammatory and toxic neuropathy, including acute infective polyneuritis, inflammatory disorders with tissue damage, HIV, hepatitis, osteoarthritis, tendovaginitis, and arthritis.

In one embodiment the treatment may be of non-immune diseases with aetiological origins in inflammatory processes including cancer, atherosclerosis, and ischaemic heart disease.

Antibody

It is an objective of the present invention to provide the use of an antibody, antigen binding fragment or recombinant protein thereof capable of selectively binding to an epitope comprising a contiguous amino acid sequence derived from interleukin-4 or a fragment, homologue or variant thereof. The invention relates to any antibody capable of selectively binding to an epitope comprising a contiguous amino acid sequence derived from interleukin-4, selected from any of the sequences set forth in SEQ ID NOS: 1-37, or a fragment or variant of said sequence.

By the term "epitope" is meant the specific group of atoms (on an antigen molecule) that is recognized by (that antigen's) antibodies. The term "epitope" is the equivalent to the term "antigenic determinant". The epitope may comprise 3 or more amino acid residues, such as for example 4, 5, 6, 7, 8 amino acid residues, located in close proximity, such as within a contiguous amino acid sequence, or located in distant parts of the amino acid sequence of an antigen, but due to protein folding have been approached to each other.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Novotny J, & Haber E. Proc Natl Acad Sci USA. 82(14):4592-6, 1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha ($\alpha$), delta ($\delta$), epsilon ($\epsilon$), gamma ($\gamma$) and mu ($\mu$), respectively. The light chains of antibodies can be assigned to one of two clearly distinct types, called kappa ($\kappa$) and lambda ($\lambda$), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely adopting a $\beta$-sheet configuration, connected by three CDRs, which form loops connecting, and in some cases forming part of, the $\beta$-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In the context of both the therapeutic and screening methods described below, preferred embodiments are the use of an antibody or fragment thereof that is immunospecific for an antigen or epitope of the invention.

The term "antibody fragment" refers to a portion of a full-length antibody, generally the antigen binding or variable region. Examples of antibody fragments include Fab, Fab', $F(ab')_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an $F(ab')_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and $F(ab')_2$ fragments.

The term "antibody fragment" is used herein interchangeably with the term "antigen binding fragment".

Antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it is has similar or immunological properties relative to antibody that binds with specificity to an epitope comprising a peptide sequence selected from any of the sequences identified herein as SEQ ID NOs: 1-37, or a fragment of said sequences. Thus, in context of the present invention the term "antibody fragment" is identical to the term "antigen binding fragment".

Antibody fragments retain some ability to selectively bind with its antigen or receptor. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

(3) $(Fab')_2$ is the fragment of an antibody that can be obtained by treating whole antibody with the enzyme pepsin without subsequent reduction.

(4) $F(ab')_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies 113: 269-315 Rosenburg and Moore eds. Springer-Verlag, N.Y., 1994.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad Sci. USA 90: 6444-6448 (1993).

The invention also contemplates multivalent antibodies having at least two binding domains. The binding domains may have specificity for the same ligand or for different ligands. In one embodiment the multispecific molecule is a bispecific antibody (BsAb), which carries at least two different binding domains, at least one of which is of antibody origin. Multivalent antibodies may be produced by a number of methods. Various methods for preparing bi- or multivalent antibodies are for example described in U.S. Pat. Nos. 5,260,203; 5,455,030; 4,881,175; 5,132,405; 5,091,513; 5,476,786; 5,013,653; 5,258,498; and 5,482,858.

The invention contemplate both polyclonal and monoclonal antibody, antigen binding fragments and recombinant proteins thereof which are capable of binding an epitope according to the invention.

The preparation of polyclonal antibodies is well-known to those skilled in the art. See, for example, Green et al. 1992. Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1, which are hereby incorporated by reference.

The preparation of monoclonal antibodies likewise is conventional. See, for example, Kohler & Milstein, Nature, 256: 495-7 (1975); Coligan, et al., sections 2.5.1-2.6.7; and Harlow, et al., in: Antibodies: A Laboratory Manual, page 726, Cold Spring Harbor Pub. (1988), Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG). In: Methods in Molecular Biology, 1992, 10:79-104, Humana Press, N.Y.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies for use with the present invention may also be isolated from phage antibody libraries using the techniques described in Clackson et al., 1991, Nature 352: 624-628, as well as in Marks et al., 1991, J Mol Biol 222: 581-597. Another method involves humanizing a monoclonal antibody by recombinant means to generate antibodies containing human specific and recognizable sequences. See, for review, Holmes, et al., 1997, J Immunol 158:2192-2201 and Vaswani, et al., 1998, Annals Allergy, Asthma & Immunol 81:105-115.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al., 1984, Proc Natl Acad Sci 81: 6851-6855.

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and U.S. Pat. No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988, Science 242:423-426; U.S. Pat. No. 4,946,778; and Pack, et al., 1993, BioTechnology 11:1271-77.

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', $F(ab')_2$ or other antigen-binding subsequences of antibodies) that contain a minimal sequence derived from non-human immunoglobulin, such as the epitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es) of the invention, such as a sequence(s) recognising an epitope(s) described herein, is one of the preferred embodiments of the invention.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., 1986, Nature 321, 522-525; Reichmann et al., 1988, Nature 332, 323-329; Presta, 1992, Curr Op Struct Biol 2:593-596; Holmes et al., 1997, J Immunol 158:2192-2201 and Vaswani, et al., 1998, Annals Allergy, Asthma & Immunol 81:105-115.

The generation of antibodies may be achieved by any standard methods in the art for producing polyclonal and monoclonal antibodies using natural or recombinant fragments of a sequence selected from any of the sequences identified as SEQ ID NOs: 1-37, as an antigen. Such antibodies may be also generated using variants or fragments of SEQ ID NOs: 1-37.

The antibodies may also be produced in vivo by the individual to be treated, for example, by administering an immunogenic fragment according to the invention to said individual. Accordingly, the present invention further relates to a vaccine comprising an immunogenic fragment described above.

The application also relates to a method for producing an antibody of the invention said method comprising a step of providing of an immunogenic fragment described above.

The invention relates both to an antibody, which is capable of modulating, such as enhancing or attenuating, biological function of IL-4 in particular a function related to inflammation, and to an antibody, which can recognise and specifically bind to IL-4 without modulating biological activity thereof.

The invention relates to use of the above antibodies for therapeutic applications involving the modulation of activity of IL-4.

In one aspect the invention relates to the use of a pharmaceutical composition comprising an antibody described above.

EXAMPLES

Example 1

Four peptides derived from IL-4 were designed and synthesized (SEQ ID NOs:1-4). Mapping of the location of the peptides was performed employing PyMOL™ software, based on PyMOL v0.99 (DeLano Scientific LLC, South San Francisco, Calif., U.S.A). This was done based on the crystal structure of the ternary complex of human Il4-Il4r-Il13ra, PDB ID: 3BPN and 3BPL (LaPorte et al., 2008).

Figure 2:
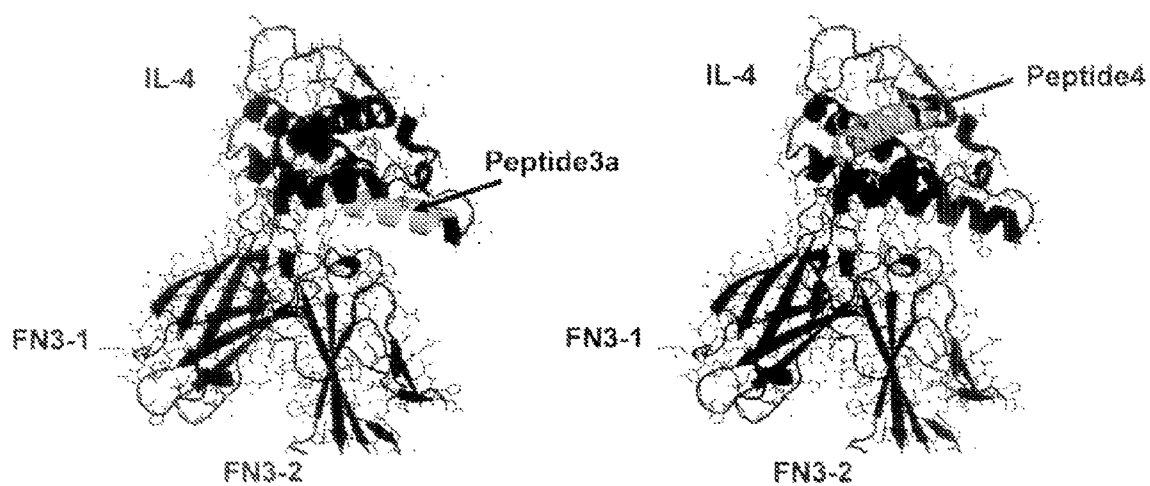
Figure 3:
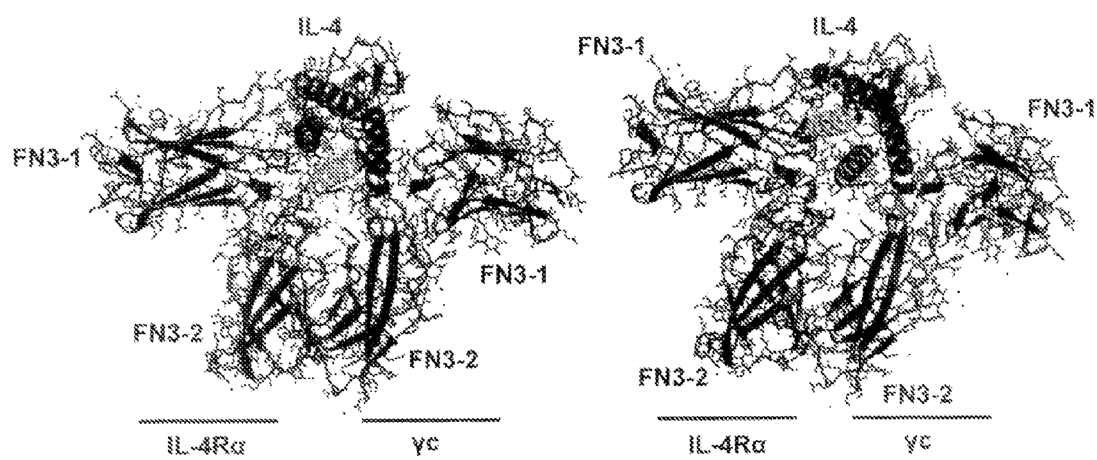
Figure 4:
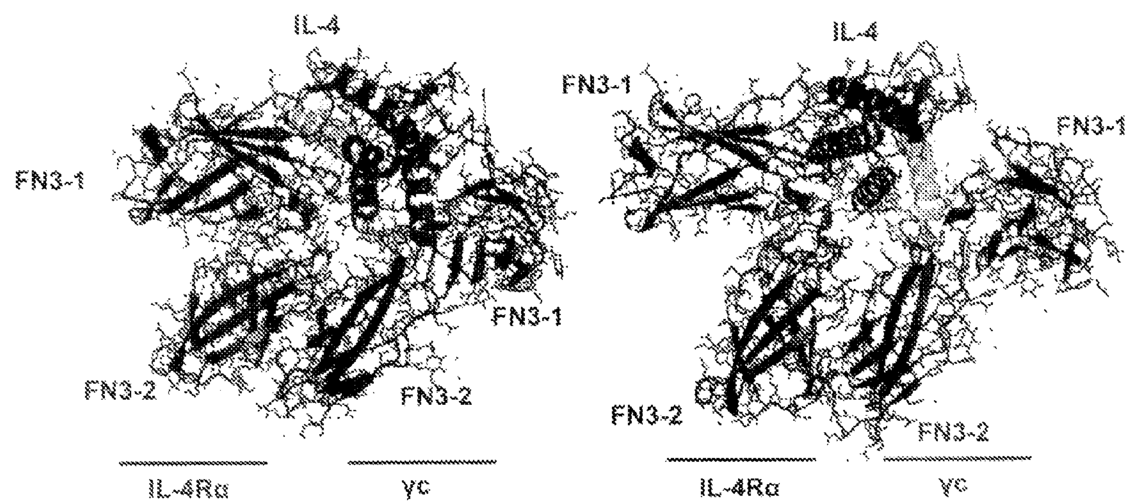
Figure 5:
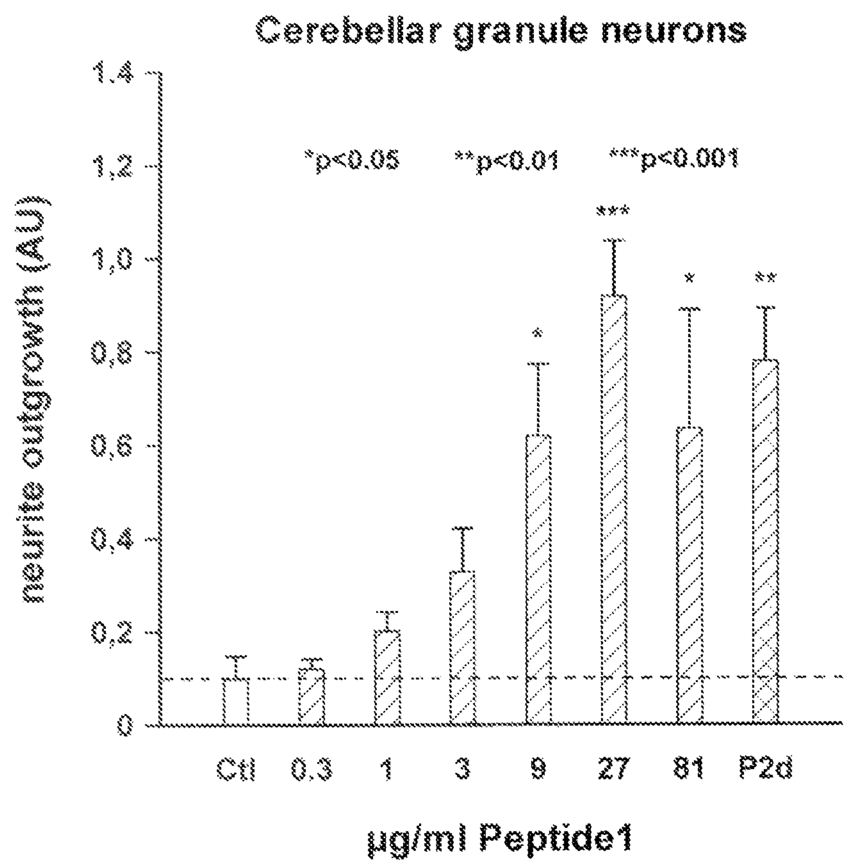
Figure 6:
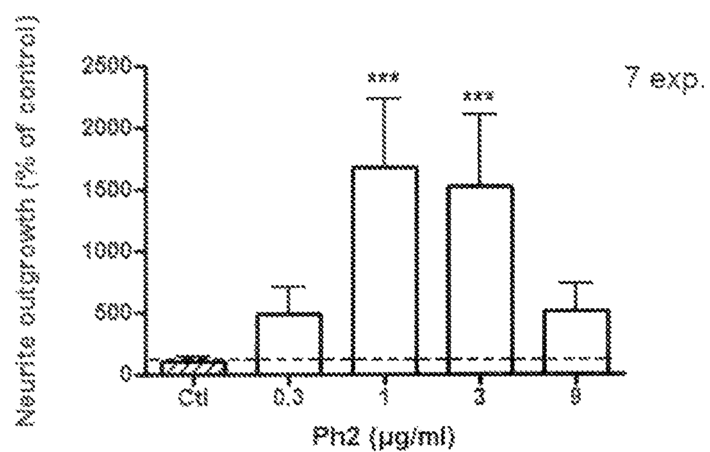
Figure 7:
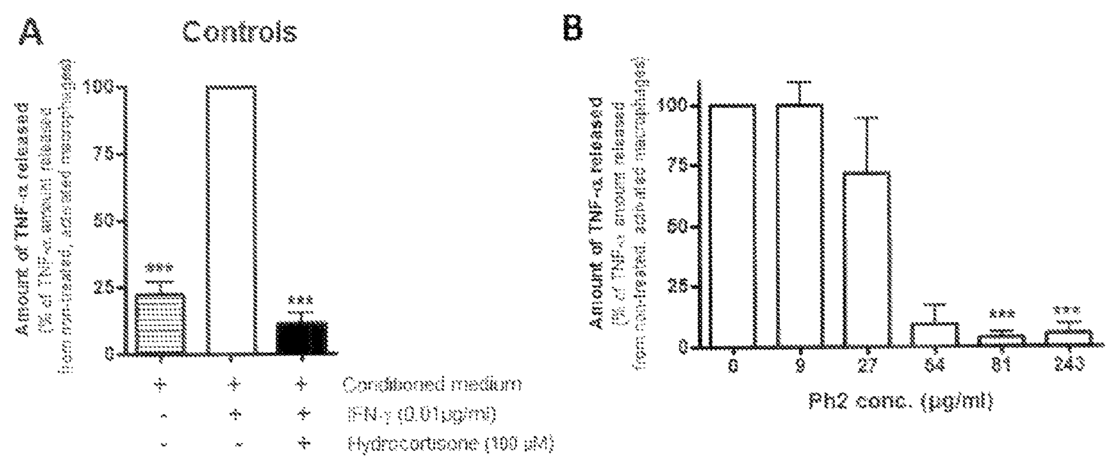

IL-4 interacts with two fibronectin type III modules (FN3-1 and FN3-2) of the extracellular part of the IL-4Rα) (FIGS. 1 and 2). IL-4 interacts with two fibronectin type III modules (FN3-1 and FN3-2) of the extracellular part of IL-4Rα and γc (FIGS. 3 and 4).

Example 2

4 peptides derived from IL-4 were tested in a neurite outgrowth assay whether they had any biological activity.

Cerebellar granular neurons (CGN) were prepared from 3 or 7 postnatal (P) day Wistar rats (Charles River, Sulzfeld, Germany or Taconic, Ejby, Denmark). Cerebella were cleared of meninges and blood vessels, roughly homogenized by chopping, and trypsinized with trypsin from Sigma-Aldrich (Brøndby, Denmark). The neurons were washed in the presence of DNAse 1 and soybean trypsin inhibitor (Sigma-Aldrich), and cellular debris was pelleted by centrifugation before plating. For single-cell culture experiments, P7 CGNs were plated at a density of 10,000 cells/well onto uncoated eight-well Lab-Tek chamber slides (NUNC, Slangerup, Denmark) in Neurobasal-A medium supplemented with 0.4% (w/v) BSA. Peptides at various concentrations were added to the medium immediately after plating, and cells were maintained at 37° C. and 5% $CO_2$ for 24 h. Cultures then were fixed, blocked and incubated with polyclonal rabbit antibody against rat GAP-43 (Chemicon, Temecula, Calif., USA) followed by incubation with secondary Alexa Fluor488 goat anti-rabbit antibody (Molecular Probes, Eugene, Oreg., USA) as previously described (Neiiendam et al., 2004). The immunostained cultures were all recorded by computer-assisted fluorescence microscopy using a Nikon Diaphot inverted microscope (Nikon, Japan) equipped with a Nikon Plane 20× objective. Images were captured with a charge-coupled device video camera (Grundig Electronics, Nurnberg, Germany) using the software package Prima developed at the Protein Laboratory (University of Copenhagen, Copenhagen, Denmark). The length of neuronal processes per cell was estimated using the software package Process Length developed at the Protein Laboratory (Ronn et al. 2000). For estimation of neurite outgrowth, at least 200±20 cells were processed for each group in each individual experiment.

Results:

Peptides with the SEQ ID NOs: 1, 2, 3, and 4, from the IL-4 binding site were found to induce a neuritogenic response from primary neurons. The results of the effect of SEQ ID NO:1 2, 3 and 4 on cerebellar neurite outgrowth are shown in FIGS. 5, 6, 9, and 12, respectively.

Example 3

Primary macrophage cells (or cells of the AMJ2C8 macrophage cell line, see Ryan et al., 1997) can be cultured for 24 h at a density of $6\times10^{-5}$ cells/ml in 12-well plates (Nunc, Slangerup, Denmark) at 37° C., in 5% $CO_2$ and 95% humidity. For determination of TNF-α release in response to LPS stimulation, triplicate cultures were cultured in DMEM with 10% FCS for 24 h and then stimulated with 0-10 μg/ml LPS for an additional 24 h period, after which culture supernatants were collected. Determination of TNF-α concentrations in conditioned media from LPS-treated macrophages was done employing the L929 fibroblast-like cells which were sensitive to TNF-α upon exposure to actinomycin D (He et al., 2002). L929 cells were seeded in 96-well plates at a density of 20.000 cells per well and maintained at 37° C., 5% $CO_2$, RPMI 1640 supplemented with 10% FCS and 0.5% penicillin-streptomycin. At 1 h prior to use as the TNF-α bioassay, L929 cells were pre-treated with 5 μg/ml actrinomycin D (Sigma), and further incubated with conditioned medium, in various dilutions, from LPS-treated macrophage cultures. Cell viability was than evaluated using the CellTiter 96 assay (Promega, Madison, Wis., USA).

Macrophage Activation Test-System

- Macrophages were seeded in 6 well multidish with 9.6 $cm^2$ per well, in the density 10.000 cells/well.
- Peptides or protein with potential anti-inflammatory effects were added to the culture. As negative control, medium was added to one well and as a positive control, 100 μM hydrocortisone was added to one well.
- Cell cultures were incubated for 24 h at 37° C.
- IFN-γ was added to the macrophage cultures to activate macrophages in the concentration 0.01 μg/ml. As control no IFN-γ but medium was added to one well.
- Fibroblast cells were seeded in a 96 well plate, in the concentration $0.2\times10^2$ cells/ml.
- Both cell cultures were incubated for 24 h at 37° C.

Conditioned medium from macrophages was collected by spinning the cell solution for 5 min at 1200 rpm. The conditioned medium was added to fibroblasts, TNF-α was added for the titration curve and finally actinomycin D was added to the fibroblasts in the concentration 0.5 μg/ml.

Results:

The effect of peptides with SEQ ID NOs:1, 3, 5, 6, and 19 on inhibition of an inflammatory response in macrophage cell cultures was tested. Results are shown in FIGS. 7, 10, and 13-17.

Example 4

Binding Studies Using Surface Plasmon Resonance (SPR) Analysis

Recombinant IL4Rα was immobilized on a CM5 sensor chip. The immobilization process was done by activating the carboxymethylated dextran matrix with 35 μl activation solution followed by an injection of protein in 10 mM sodium acetate solution (pH 5.0). After a desired level of protein was immobilized 35 μl of deactivation solution is injected to deactivate any free carboxymethylated groups in the dextran matrix. One flow cell was always empty as a control. Each analyte (recombinant IL-4 or IL-4-derived peptides) was diluted in PBS and injected at a flow rate of 10 μl/min. The obtained data was analyzed by performing a non-linear curve fitting using the software BIAevaluation v.4 from Biacore. The curves were fitted to a 1:1 Langmuir binding model which describes the interaction of two molecules in 1:1 complex. The affinity constant ($K_D$) was calculated from the association rate constant ($k_a$) and the dissociation rate constant ($k_d$). This was done by using the following formula, where L is the immobilized ligand, A the analyte, and LA is the analyte-ligand complex:

$$\text{Langmuir 1:1 model: } L + \frac{k_a \rightarrow}{\leftarrow k_d} LA$$

Rate of Decreasing Ligand Concentration $$\frac{d[L]}{dt} = -(k_a * [L] * [A] - k_d * [LA])$$

Rate of Increasing Product Concentration $$\frac{d[LA]}{dt} = k_a * [L] * [A] - k_d * [LA]$$

At Steady State $$\frac{d[LA]}{dt} = 0$$

$$\Rightarrow k_a * [L] * [A] - k_d * [LA] = 0$$

$$\Rightarrow \frac{[L]*[A]}{[LA]} = \frac{k_d}{k_a} = K_D$$

Figure 8:
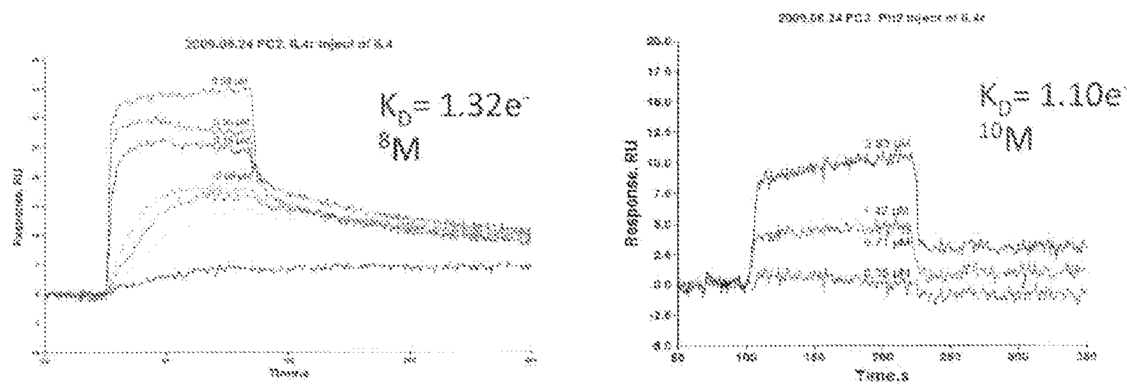
Figure 9:
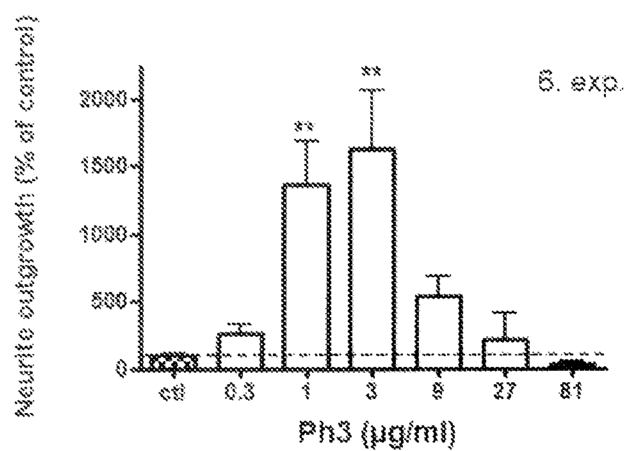
Figure 10:
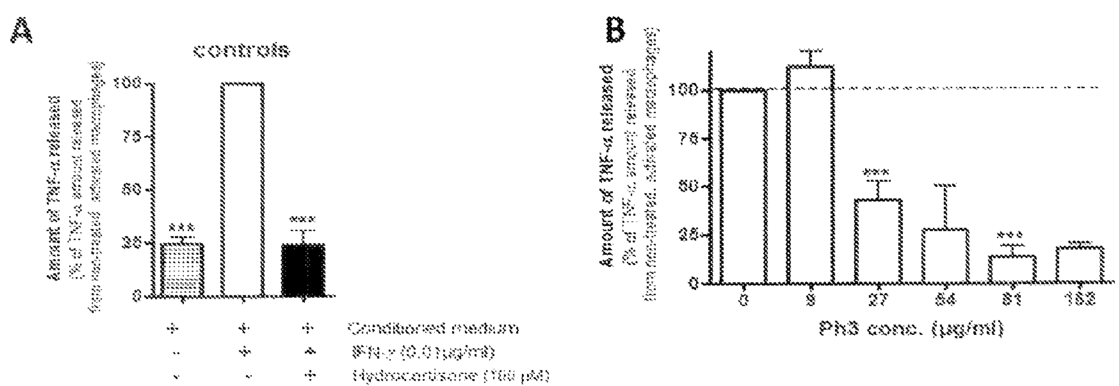
Figure 11:
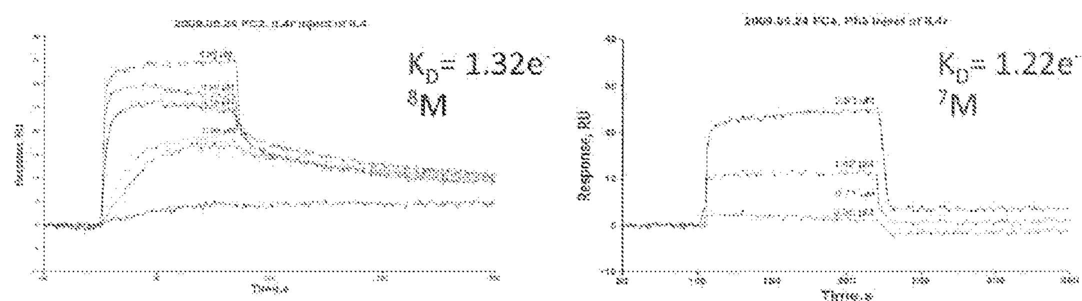
Figure 12:
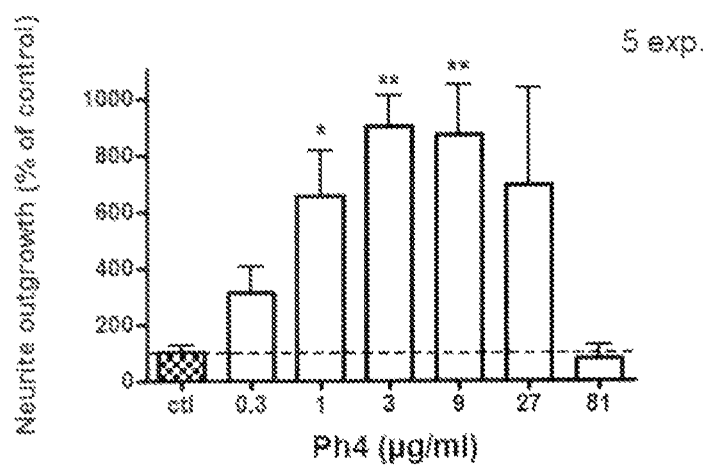
Figure 13:
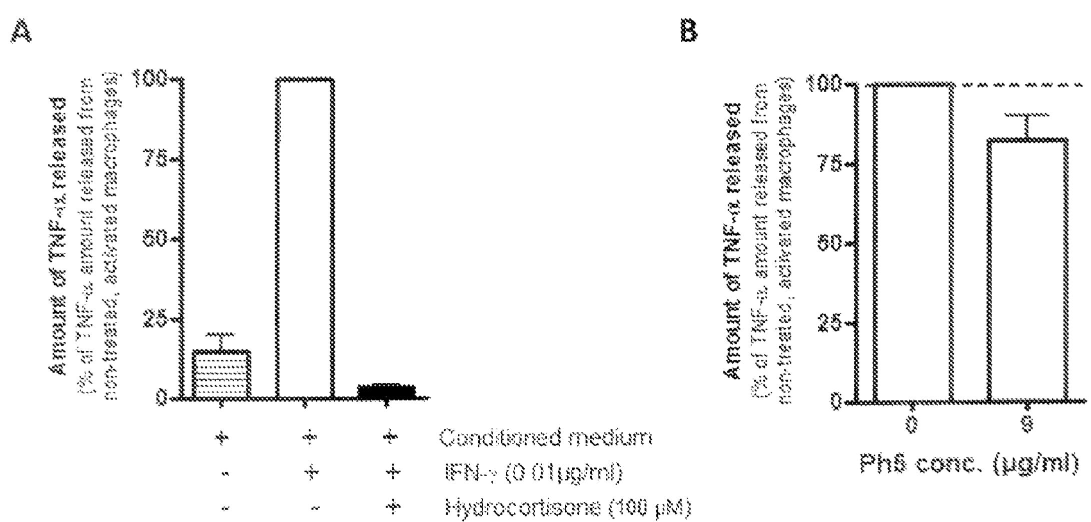
Figure 14:
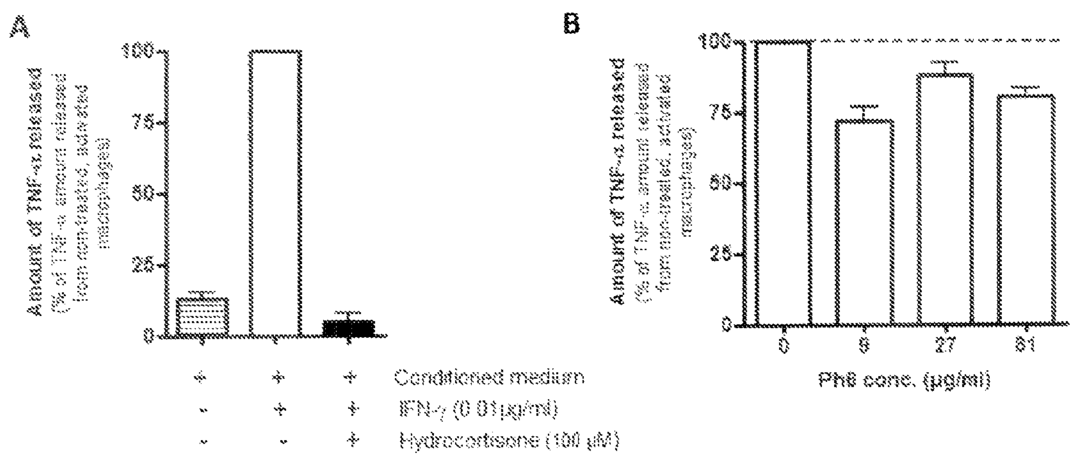
Figure 15:
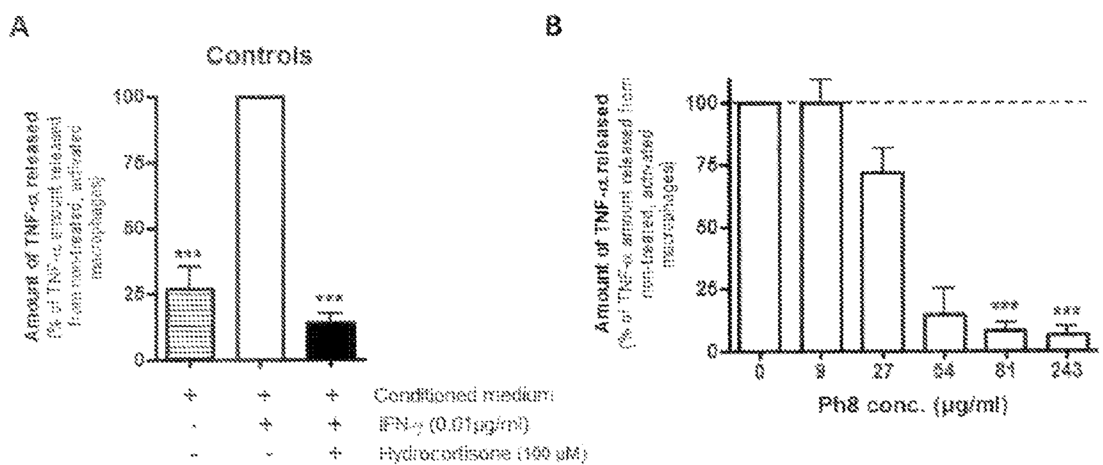
Figure 16:
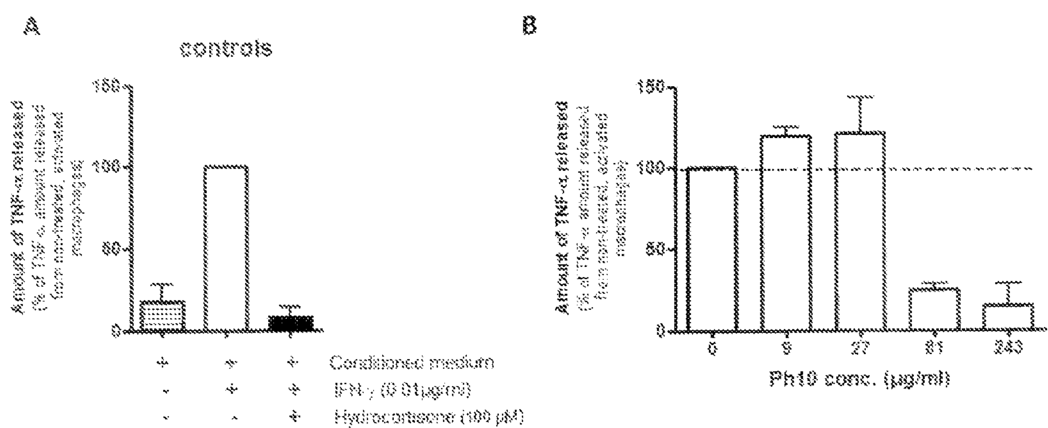
Figure 17:
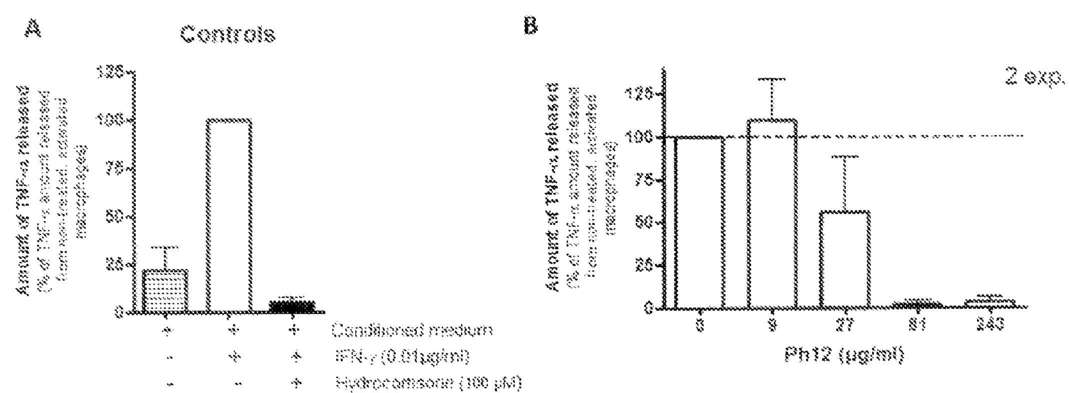

Results:

Binding between Ph2 (SEQ ID NO:3), and IL4rα, and between Ph3 (SEQ ID NO:1) and IL4rα was studied. The results are shown in FIGS. 8 and 11, respectively.

REFERENCES

Agnello D, Lankford C S, Bream J, Morinobu A, Gadina M, O'Shea J J, Frucht D M. Cytokines and transcription factors that regulate T helper cell differentiation: new players and new insights. J Clin Immunol. 2003, 23, 147-61.

Hage T, Sebald W, Reinemer P. Crystal structure of the interleukin-4/receptor α chain complex reveals a mosaic binding interface. Cell 1999, 97, 271-281.

He B P, Wen W, Strong M J. Activated microglia (BV-2) facilitatation of TNF-α-mediated motor meuron death in vitro. J Immunol. 2002, 128, 31-38.

Izuhara K, Arima K, Yasunaga S. IL-4 and IL13: Their patological roles in allergic diseases and their potencial in developing new therapies. Curr Drug Targets-Inflam Allergy 2002, 1 263-269.

Leach M W, Mary Ellen Rybak M E, Rosenblum I Y. Safety Evaluation of Recombinant Human Interleukin-4. Clin Immunol Immunopathol. 1997, 83, 12-14.

Martin R. Interleukin 4 treatment of psoriasis: are pleiotropic cytokines suitable therapies for autoimmune diseases? TRENDS Pharmacol Sci. 2003, 24, 613-616.

Martinez F O, Sica A, Mantovani A, Locati M. Macrophage activation and polarization. Front Biosci. 2008, 13, 453-61.

Muller T, Oehlenschlager F, Buehner M. Human interleukin-4 and variant R88Q: phasing X-ray diffraction data by molecular replacement using X-ray and nuclear magnetic resonance models. 1995, 247, 360-372.

Neiiendam J, Køhler L, Christensen C, Li S, Pedersen M V, Ditlevsen D, Kornum M, Kiselyov V, Berezin V, Bock E. An NCAM-derived FGF-receptor agonist, the FGL-peptide, induces neurite outgrowth and neuronal survival in primary rat neurons. J. Neurochem. 2004, 91, 920-935.

LaPorte S L, Juo Z S, Vaclavikova J, CoIf L A, Qi X, Heller N M, Keegan A D, Garcia K C. Molecular and structural basis of cytokine receptor pleiotropy in the interleukin-4/13 system. Cell 2008, 132, 259-272.

Rønn L C B, Ralets I, Hartz B, Bech M, Berezin A, Berezin V, Møller A, Bock, E A simple procedure for quantification of neurite outgrowth based on stereological principles. J. Neurosci. Methods 2000, 100, 25-32.

Ryan L K, Colenbock D T, Wu J, Vermeulen M W. Characterization of proinflammatory cytokine production and CD14 expression by murine alveolar macrophage cell lines. In Vitro Cell Dev Biol Anim. 1997, 33, 647-653.

Soroka V, Kiryushko D, Novitskaya V, Ronn L C, Poulsen F M, Holm A, Bock E and Berezin V. Induction of neuronal differentiation by a peptide corresponding to the homophilic binding site of the second Ig module of NCAM. J. Biol. Chem. 2002, 277, 24676-24683.

Szegedi A, Aleksza M, Gonda A, Irinyi B, Sipka S, Hunyadi J, Antal-Szalmás P. Elevated rate of Thelperl (T(H)1) lymphocytes and serum IFN-gamma levels in psoriatic patients. Immunol Lett. 2003, 86, 277-80.

Whitehead R P, Unger J M, Goodwin J W, Walker M J, Thompson J A, Flaherty L E, Sondak V K. Phase II trial of recombinant human interleukin-4 in patients with disseminated malignant melanoma: a Southwest Oncology Group study. J Imminother. 1998, 21, 440-446.

The invention claimed is:

1. A method for treatment of inflammatory diseases or conditions comprising administration, to an individual in need thereof, of a compound having one or more peptides, each peptide consisting of a sequence selected from the group consisting of

```
AQFHRHKQLIRFLKRA        (SEQ ID NO: 1),

RNKQVIDSLAKFLKR         (SEQ ID NO: 19),

ARFLKRLDRNLWGG          (SEQ ID NO: 3),

KRLQQNLFGG              (SEQ ID NO: 6),
and

Ac-AQFHRHKQLIRFLKRA     (SEQ ID NO: 7),
```

or a variant of said sequence, said variant being substituted at 1 amino acid position with a conservative amino acid substitution, wherein said compound is capable of decreasing LPS-induced TNF-alpha release by macrophages.

2. A compound comprising an isolated peptide sequence consisting of one of the following sequences

```
AQFHRHKQLIRFLKRA        (SEQ ID NO: 1),

RNKQVIDSLAKFLKR         (SEQ ID NO: 19),

ARFLKRLDRNLWGG          (SEQ ID NO: 3),

KRLQQNLFGG              (SEQ ID NO: 6),
and

Ac-AQFHRHKQLIRFLKRA     (SEQ ID NO: 7),
```

or a variant thereof, said variant being substituted at 1 amino acid position with a conservative amino acid substitution, wherein said compound is capable of decreasing LPS-induced TNF-alpha release by macrophages.

3. A pharmaceutical composition comprising at least one compound as defined in claim 2.

4. The method according to claim 1, wherein the inflammatory disease or condition is an autoimmune disease or condition.

5. The method according to claim 1, wherein the inflammatory disease or condition is rheumatoid arthritis.

6. The method according to claim 1, wherein the compound is formulated for subcutaneous, intravenous, oral, nasal, pulmonal, topical parenteral and/or intraarticular administration.

7. The method according to claim 1, wherein said one or more peptides consists of a monomer of one peptide sequence.

8. The method according to claim 1, wherein said compound comprises a multimer of two or more copies of the same peptide sequence.

9. The method according to claim 1, wherein said peptide is capable of activating B-cells, and/or activating growth and survival of T-cells, and/or down-regulating C5a and C3a in monocytes and dendritic cells, and/or inhibiting macrophage activation.

10. The method according to claim 1, wherein said peptide consists of AQFHRHKQLIRFLKRA (SEQ ID NO:1).

11. The method according to claim 1, wherein said peptide consists of RNKQVIDSLAKFLKR (SEQ ID NO:19).

12. The method according to claim 1, wherein the inflammatory disease or condition is ischemic heart disease.

13. The method according to claim 1, wherein said peptide consists of ARFLKRLDRNLWGG (SEQ ID NO:3).

14. The method according to claim 1, wherein said peptide consists of KRLQQNLFGG (SEQ ID NO:6).

15. The method according to claim 1, wherein said peptide consists of Ac-AQFHRHKQLIRFLKRA (SEQ ID NO:7).

* * * * *

SEQUENCE LISTING

```
<160> NUMBER OF SEQ ID NOS: 38

<210> SEQ ID NO 1
<211> LENGTH: 16
<212> TYPE: PRT
<213> ORGANISM: Artificial Sequence
<220> FEATURE:
<223> OTHER INFORMATION: Variant of fragment of interleukin-4

<400> SEQUENCE: 1

Ala Gln Phe His Arg His Lys Gln Leu Ile Arg Phe Leu Lys Arg Ala
1               5                   10                  15


<210> SEQ ID NO 2
<211> LENGTH: 14
<212> TYPE: PRT
<213> ORGANISM: Artificial Sequence
<220> FEATURE:
<223> OTHER INFORMATION: Variant of fragment of interleukin-4

<400> SEQUENCE: 2

Ala Ile Thr Leu Gln Glu Ile Ile Lys Thr Leu Asn Ser Ala
1               5                   10


<210> SEQ ID NO 3
<211> LENGTH: 14
<212> TYPE: PRT
<213> ORGANISM: Artificial Sequence
<220> FEATURE:
<223> OTHER INFORMATION: Variant of fragment of interleukin-4

<400> SEQUENCE: 3

Ala Arg Phe Leu Lys Arg Leu Asp Arg Asn Leu Trp Gly Gly
1               5                   10


<210> SEQ ID NO 4
<211> LENGTH: 15
<212> TYPE: PRT
<213> ORGANISM: Artificial Sequence
<220> FEATURE:
```

<223> OTHER INFORMATION: Variant of fragment of interleukin-4

<400> SEQUENCE: 4

```
Ala Glu Arg Leu Lys Thr Ile Met Arg Glu Lys Tyr Ser Lys Ser
1               5                   10                  15
```

<210> SEQ ID NO 5
<211> LENGTH: 8
<212> TYPE: PRT
<213> ORGANISM: Artificial Sequence
<220> FEATURE:
<223> OTHER INFORMATION: Variant of fragment of interleukin-4

<400> SEQUENCE: 5

```
Leu Gln Glu Ile Lys Thr Leu Asn
1               5
```

<210> SEQ ID NO 6
<211> LENGTH: 10
<212> TYPE: PRT
<213> ORGANISM: Artificial Sequence
<220> FEATURE:
<223> OTHER INFORMATION: Variant of fragment of interleukin-4

<400> SEQUENCE: 6

```
Lys Arg Leu Gln Gln Asn Leu Phe Gly Gly
1               5                   10
```

<210> SEQ ID NO 7
<211> LENGTH: 18
<212> TYPE: PRT
<213> ORGANISM: Artificial Sequence
<220> FEATURE:
<223> OTHER INFORMATION: Variant of fragment of interleukin-4

<400> SEQUENCE: 7

```
Ala Cys Ala Gln Phe His Arg His Lys Gln Leu Ile Arg Phe Leu Lys
1               5                   10                  15

Arg Ala
```

<210> SEQ ID NO 8
<211> LENGTH: 7
<212> TYPE: PRT
<213> ORGANISM: Artificial Sequence
<220> FEATURE:
<223> OTHER INFORMATION: Variant of fragment of interleukin-4

<400> SEQUENCE: 8

```
Gln Glu Ile Ile Lys Lys Leu
1               5
```

<210> SEQ ID NO 9
<211> LENGTH: 13
<212> TYPE: PRT
<213> ORGANISM: Artificial Sequence
<220> FEATURE:
<223> OTHER INFORMATION: Variant of fragment of interleukin-4

<400> SEQUENCE: 9

```
Ala Ile Gln Asn Gln Glu Glu Ile Lys Tyr Leu Asn Ser
1               5                   10
```

<210> SEQ ID NO 10
<211> LENGTH: 7
<212> TYPE: PRT
<213> ORGANISM: Artificial Sequence
<220> FEATURE:

<223> OTHER INFORMATION: Variant of fragment of interleukin-4

<400> SEQUENCE: 10

Ala Ile Ile Leu Gln Glu Ile
1               5

<210> SEQ ID NO 11
<211> LENGTH: 7
<212> TYPE: PRT
<213> ORGANISM: Artificial Sequence
<220> FEATURE:
<223> OTHER INFORMATION: Variant of fragment of interleukin-4

<400> SEQUENCE: 11

Ile Val Leu Gln Glu Ile Ile
1               5

<210> SEQ ID NO 12
<211> LENGTH: 11
<212> TYPE: PRT
<213> ORGANISM: Artificial Sequence
<220> FEATURE:
<223> OTHER INFORMATION: Variant of fragment of interleukin-4

<400> SEQUENCE: 12

Thr Leu Gly Glu Ile Ile Lys Gly Val Asn Ser
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Variant of fragment of interleukin-4

<400> SEQUENCE: 13

Val Thr Leu Ile Asp His Ser Glu Glu Ile Phe Lys Thr Leu Asn
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: Variant of fragment of interleukin-4

<400> SEQUENCE: 14

Leu Gln Glu Arg Ile Lys Ser Leu Asn
1               5

<210> SEQ ID NO 15
<211> LENGTH: 13
<212> TYPE: PRT
<213> ORGANISM: Artificial Sequence
<220> FEATURE:
<223> OTHER INFORMATION: Variant of fragment of interleukin-4

<400> SEQUENCE: 15

Arg Leu Asp Arg Glu Asn Val Ala Val Tyr Asn Leu Trp
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Variant of fragment of interleukin-4

<400> SEQUENCE: 16

Leu Arg Ser Leu Asp Arg Asn Leu
1 5

<210> SEQ ID NO 17
<211> LENGTH: 8
<212> TYPE: PRT
<213> ORGANISM: Artificial Sequence
<220> FEATURE:
<223> OTHER INFORMATION: Variant of fragment of interleukin-4

<400> SEQUENCE: 17

Arg Leu Leu Arg Leu Asp Arg Asn
1 5

<210> SEQ ID NO 18
<211> LENGTH: 14
<212> TYPE: PRT
<213> ORGANISM: Artificial Sequence
<220> FEATURE:
<223> OTHER INFORMATION: Variant of fragment of interleukin-4

<400> SEQUENCE: 18

Arg Phe Leu Lys Arg Tyr Phe Tyr Asn Leu Glu Glu Asn Leu
1 5 10

<210> SEQ ID NO 19
<211> LENGTH: 15
<212> TYPE: PRT
<213> ORGANISM: Artificial Sequence
<220> FEATURE:
<223> OTHER INFORMATION: Variant of fragment of interleukin-4

<400> SEQUENCE: 19

Arg Asn Lys Gln Val Ile Asp Ser Leu Ala Lys Phe Leu Lys Arg
1 5 10 15

<210> SEQ ID NO 20
<211> LENGTH: 7
<212> TYPE: PRT
<213> ORGANISM: Artificial Sequence
<220> FEATURE:
<223> OTHER INFORMATION: Variant of fragment of interleukin-4

<400> SEQUENCE: 20

Arg His Lys Ala Leu Ile Arg
1 5

<210> SEQ ID NO 21
<211> LENGTH: 8
<212> TYPE: PRT
<213> ORGANISM: Artificial Sequence
<220> FEATURE:
<223> OTHER INFORMATION: Variant of fragment of interleukin-4

<400> SEQUENCE: 21

Lys Lys Leu Ile Arg Tyr Leu Lys
1 5

<210> SEQ ID NO 22
<211> LENGTH: 7
<212> TYPE: PRT
<213> ORGANISM: Artificial Sequence
<220> FEATURE:
<223> OTHER INFORMATION: Variant of fragment of interleukin-4

<400> SEQUENCE: 22

Arg His Lys Thr Leu Ile Arg
1 5

<210> SEQ ID NO 23
<211> LENGTH: 8
<212> TYPE: PRT
<213> ORGANISM: Artificial Sequence
<220> FEATURE:
<223> OTHER INFORMATION: Variant of fragment of interleukin-4

<400> SEQUENCE: 23

Met Gln Asp Lys Tyr Ser Lys Ser
1 5

<210> SEQ ID NO 24
<211> LENGTH: 15
<212> TYPE: PRT
<213> ORGANISM: Artificial Sequence
<220> FEATURE:
<223> OTHER INFORMATION: Variant of fragment of interleukin-4

<400> SEQUENCE: 24

Ala Glu Arg Val Lys Ile Glu Gln Arg Glu Tyr Lys Lys Tyr Ser
1 5 10 15

<210> SEQ ID NO 25
<211> LENGTH: 11
<212> TYPE: PRT
<213> ORGANISM: Artificial Sequence
<220> FEATURE:
<223> OTHER INFORMATION: Variant of fragment of interleukin-4

<400> SEQUENCE: 25

Ser Gln Leu Ile Arg Phe Leu Lys Arg Leu Ala
1 5 10

<210> SEQ ID NO 26
<211> LENGTH: 13
<212> TYPE: PRT
<213> ORGANISM: Artificial Sequence
<220> FEATURE:
<223> OTHER INFORMATION: Variant of fragment of interleukin-4

<400> SEQUENCE: 26

Thr Val Thr Asp Ile Phe Ala Ala Ser Lys Asn Thr Thr
1 5 10

<210> SEQ ID NO 27
<211> LENGTH: 12
<212> TYPE: PRT
<213> ORGANISM: Artificial Sequence
<220> FEATURE:
<223> OTHER INFORMATION: Variant of fragment of interleukin-4

<400> SEQUENCE: 27

Thr Leu Glu Asn Phe Leu Glu Arg Leu Lys Thr Ala
1 5 10

<210> SEQ ID NO 28
<211> LENGTH: 12
<212> TYPE: PRT
<213> ORGANISM: Artificial Sequence
<220> FEATURE:
<223> OTHER INFORMATION: Variant of fragment of interleukin-4

<400> SEQUENCE: 28

Thr Glu Lys Glu Val Leu Arg Gln Phe Tyr Ser Ala
1 5 10

<210> SEQ ID NO 29
<211> LENGTH: 12
<212> TYPE: PRT
<213> ORGANISM: Artificial Sequence
<220> FEATURE:
<223> OTHER INFORMATION: Variant of fragment of interleukin-4

<400> SEQUENCE: 29

Lys Thr Leu Thr Glu Leu Thr Lys Thr Leu Asn Ser
1 5 10

<210> SEQ ID NO 30
<211> LENGTH: 15
<212> TYPE: PRT
<213> ORGANISM: Artificial Sequence
<220> FEATURE:
<223> OTHER INFORMATION: Variant of fragment of interleukin-4

<400> SEQUENCE: 30

Ala His Lys Glu Ile Ile Lys Thr Leu Asn Ser Leu Gln Lys Ala
1 5 10 15

<210> SEQ ID NO 31
<211> LENGTH: 12
<212> TYPE: PRT
<213> ORGANISM: Artificial Sequence
<220> FEATURE:
<223> OTHER INFORMATION: Variant of fragment of interleukin-4

<400> SEQUENCE: 31

Ala Lys Thr Leu Ser Thr Glu Leu Thr Val Thr Ala
1 5 10

<210> SEQ ID NO 32
<211> LENGTH: 11
<212> TYPE: PRT
<213> ORGANISM: Artificial Sequence
<220> FEATURE:
<223> OTHER INFORMATION: Variant of fragment of interleukin-4

<400> SEQUENCE: 32

Ser Thr Leu Glu Asn Phe Leu Glu Arg Leu Ala
1 5 10

<210> SEQ ID NO 33
<211> LENGTH: 11
<212> TYPE: PRT
<213> ORGANISM: Artificial Sequence
<220> FEATURE:
<223> OTHER INFORMATION: Variant of fragment of interleukin-4

<400> SEQUENCE: 33

Asn Glu Glu Arg Leu Lys Thr Ile Met Arg Ala
1 5 10

<210> SEQ ID NO 34
<211> LENGTH: 12
<212> TYPE: PRT
<213> ORGANISM: Artificial Sequence
<220> FEATURE:
<223> OTHER INFORMATION: Variant of fragment of interleukin-4

<400> SEQUENCE: 34

Arg Ala Ala Thr Val Leu Arg Gln Phe Tyr Ser Arg
1 5 10

<210> SEQ ID NO 35
<211> LENGTH: 11
<212> TYPE: PRT
<213> ORGANISM: Artificial Sequence
<220> FEATURE:
<223> OTHER INFORMATION: Variant of fragment of interleukin-4

<400> SEQUENCE: 35

```
Lys Thr Leu Asn Ser Leu Thr Glu Gln Lys Thr
1               5                   10
```

<210> SEQ ID NO 36
<211> LENGTH: 10
<212> TYPE: PRT
<213> ORGANISM: Artificial Sequence
<220> FEATURE:
<223> OTHER INFORMATION: Variant of fragment of interleukin-4

<400> SEQUENCE: 36

```
Ala His Arg His Lys Gln Leu Ile Arg Ala
1               5                   10
```

<210> SEQ ID NO 37
<211> LENGTH: 12
<212> TYPE: PRT
<213> ORGANISM: Artificial Sequence
<220> FEATURE:
<223> OTHER INFORMATION: Variant of fragment of interleukin-4

<400> SEQUENCE: 37

```
Ala Thr Ala Gln Gln Phe His Arg His Lys Gln Ala
1               5                   10
```

<210> SEQ ID NO 38
<211> LENGTH: 153
<212> TYPE: PRT
<213> ORGANISM: Human
<220> FEATURE:
<221> NAME/KEY: MISC_FEATURE
<223> OTHER INFORMATION: Human interleukin-4

<400> SEQUENCE: 38

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```